(12) United States Patent
Bashiardes et al.

(10) Patent No.: US 6,399,613 B1
(45) Date of Patent: Jun. 4, 2002

(54) PYRAZINE DERIVATIVES, THEIR PREPARATION AND MEDICAMENTS CONTAINING THEM

(75) Inventors: Georges Bashiardes, Poitiers; Jean-Christophe Carry, Meudon; Michel Evers, La Queue en Brie; Bruno Filoche, Creteil; Serge Mignani, Chatenay-Malabry, all of (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/483,984

(22) Filed: Jan. 14, 2000

Related U.S. Application Data

(63) Continuation of application No. PCT/FR98/01542, filed on Jul. 15, 1998.

(30) Foreign Application Priority Data

Jul. 17, 1997 (FR) .............................. 97 09058

(51) Int. Cl.⁷ ........................ A61K 31/50; C07D 241/02
(52) U.S. Cl. .................... 514/252.1; 544/336; 544/387; 514/183
(58) Field of Search .............................. 514/252.1, 183; 544/336, 387

(56) References Cited

FOREIGN PATENT DOCUMENTS

| DE | 2222934 | * | 11/1972 |
|----|---------|---|---------|
| DE | 3703959 |   | 8/1988  |
| EP | 0010896 | * | 5/1980  |
| EP | 0463592 |   | 1/1992  |

OTHER PUBLICATIONS

Chemical Abstracts, vol. 111, No. 21, Nov. 20, 1989, Columbus, Ohio, US; abstract No. 194802s, (= JP 0117 863 [89117 863].

Grootenhuis et al., "Complexes of macromolecular polyethers and neutral guest molecules: a systematic approach to the complexation of water molecules by 2,6–pyridinium crown ethers.", J. Am. Chem. Soc. 108(4):780–788 (1996).

Kumar et al., Synthetic ionophores part 14: effect of pyridine and thioehter ligating units on Ag selectivity in 18–membered diamide–diester macrocycles., Tetrahedron 52(42):13483–13492 (1996).

International Preliminary Examination Report for PCT/FR98/01542.

* cited by examiner

Primary Examiner—Richard L. Raymond
Assistant Examiner—Sudhaker B. Patel
(74) Attorney, Agent, or Firm—Irving Newman

(57) ABSTRACT

The invention concerns pyrazine derivatives of formula (1) in which a pharmaceutical composition comprising at least one compound of formula:

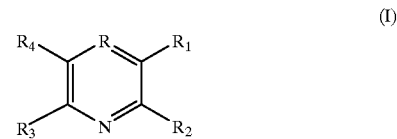

in which
R represents a nitrogen atom, $R_1$ and $R_3$ each represent the same radical selected from the group consisting of —CO—$NR_5R_6$, —CO—N(CH($CH_2OH$)$_2$)$_2$, —CO—N($CH_2OH$)$_2$, —CO—N($CH_2$—CH($CH_2OH$)$_2$)$_2$, —CO—N($CH_2$—(CHOH)$_n$—$CH_2OH$)$_2$ in which n is equal to 0, 1, 2, 3 or 4, —$CH_2$—O—$R_6$, —$NR_5$—CO—$R_6$, —$CH_2$—$NR_5R_6$, —$CH_2$—N($CH_2OH$)$_2$, —$CH_2$—N($CH_2$—(CHOH)$_y$—$CH_2OH$)$_2$ in which y is equal to 0, 1, 2, 3 or 4, —$CH_2$—N(CH($CH_2OH$)$_2$)$_2$ and —$CH_2$—N($CH_2$—CH($CH_2OH$)$_2$)$_2$ and $R_2$ and $R_4$ each represents a hydrogen atom, $R_5$ represents a hydrogen atom or an alkyl radical, $R_6$ represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$, —C($CH_2OH$)$_3$, —C($CH_3$)($CH_2OH$)$_2$, —$CH_2$—CH($CH_2OH$)$_2$ or —CH($CH_2OH$)—(CHOH)$_x$—$CH_2OH$ in which x is equal to 1, 2, 3 or 4, alk represents an alkyl radical, the alkyl radicals containing, unless otherwise stated, 1 to 6 carbon atoms in a straight or branched chain, stereoisomers thereof and salts thereof with an inorganic or organic acid and their preparation.

9 Claims, No Drawings

PYRAZINE DERIVATIVES, THEIR PREPARATION AND MEDICAMENTS CONTAINING THEM

This application is a continuation of PCT/FR98/01542 filed Jul. 15, 1998.

The present invention relates to medicaments containing, as active principle, a compound of formula:

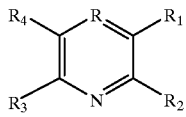

(I)

a stereoisomer or a salt of such a compound with an inorganic or organic acid, to the novel compounds of formula (I) and to a process for their preparation.

In formula (I) either

R represents a nitrogen atom, $R_1$ represents a radical —CO—$NR_5R_6$, —CO—N(CH($CH_2OH)_2)_2$, —CO—N($CH_2OH)_2$, —CO—N($CH_2$—CH($CH_2OH)_2)_2$, —CO—N($CH_2$—(CHOH)$_n$—$CH_2OH)_2$ in which n is equal to 0, 1, 2, 3 or 4, —$CH_2$—O—$R_6$, —$NR_5$—CO—$R_6$, —$CH_2$—$NR_5R_6$, —$CH_2$—N ($CH_2OH)_2$, —$CH_2$—N($CH_2$—(CHOH)$_y$—$CH_2OH)_2$ in which y is equal to 0, 1, 2, 3 or 4, —$CH_2$—N(CH($CH_2OH)_2)_2$ or —$CH_2$—N($CH_2$—CH($CH_2OH)_2)_2$ and one of the substituents $R_3$ or $R_4$ represents a hydrogen atom and the other is identical to $R_1$ and $R_2$ represents a hydrogen atom, or R represents a CH residue, $R_1$ and $R_4$ are identical and each represent a radical —CO—$NR_5R_6$, —CO—N(CH($CH_2OH)_2)_2$, —CO—N($CH_2OH)_2$, —CO—N($CH_2$—CH($CH_2OH)_2)_2$, —CO—N($CH_2$—(CHOH)$_n$—$CH_2OH)_2$ in which n is equal to 0, 1, 2, 3 or 4, —$CH_2$—O—$R_6$, —$NR_5$—CO—$R_6$, —$CH_2$—$NR_5R_6$, —$CH_2$—N($CH_2OH)_2$, —$CH_2$—N($CH_2$—(CHOH)$_y$—$CH_2OH)_2$ in which y is equal to 0, 1, 2, 3 or 4, —$CH_2$—N(CH($CH_2OH)_2)_2$ or —$CH_2$—N($CH_2$—CH($CH_2OH)_2)_2$ and $R_2$ and $R_3$ each represent a hydrogen atom, or R represents a CH residue, $R_1$ and $R_3$ are identical and each represent a radical —CO—$NR_5R_6$, —CO—N(CH($CH_2OH)_2)_2$, —CO—N($CH_2OH)_2$, —CO—N($CH_2$—CH($CH_2OH)_2)_2$, —CO—N($CH_2$—(CHOH)$_n$—$CH_2OH)_2$ in which n is equal to 0, 1, 2, 3 or 4, —$CH_2$—O—$R_6$, —$NR_5$—CO—$R_6$, —$CH_2$—$NR_5R_6$, —$CH_2$—N($CH_2OH)_2$, —$CH_2$—N($CH_2$—(CHOH)$_y$—$CH_2OH)_2$ in which y is equal to 0, 1, 2, 3 or 4, —$CH_2$—N(CH($CH_2OH)_2)_2$ or —$CH_2$—N($CH_2$—CH($CH_2OH)_2)_2$ and $R_2$ and $R_4$ each represent a hydrogen atom, or R represents a CH residue, $R_2$ and $R_3$ are identical and each represent a radical —CO—$NR_5R_6$, —CO—N(CH($CH_2OH)_2)_2$, —CO—N($CH_2OH)_2$, —CO—N($CH_2$—CH($CH_2OH)_2)_2$, —CO—N($CH_2$—(CHOH)$_n$—$CH_2OH)_2$ in which n is equal to 0, 1, 2, 3 or 4, —$CH_2$—O—$R_6$, —$NR_5$—CO—$R_6$, —$CH_2$—$NR_5R_6$, —$CH_2$—N($CH_2OH)_2$, —$CH_2$—N($CH_2$—(CHOH)$_y$—$CH_2OH)_2$ in which y is equal to 0, 1, 2, 3 or 4, —$CH_2$—N(CH($CH_2OH)_2)_2$ or —$CH_2$—N($CH_2$—CH($CH_2OH)_2)_2$ and $R_1$ and $R_4$ each represent a hydrogen atom, $R_5$ represents a hydrogen atom or an alkyl radical, $R_6$ represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH)_2$, —C($CH_2OH)_3$, —C($CH_3$) ($CH_2OH)_2$, —$CH_2$—CH($CH_2OH)_2$ or —CH($CH_2OH$)—(CHOH)$_x$—$CH_2OH$ in which x is equal to 1, 2, 3 or 4, alk represents an alkyl radical.

In the definitions hereinabove and in those hereinbelow, the alkyl radicals contain 1 to 6 carbon atoms in a straight or branched chain.

The compounds of formula (I) containing asymmetric carbon atoms have stereoisomeric forms. These stereoisomers form part of the invention.

The preferred medicaments are those which contain a compound of formula (I) chosen from the following compounds:

N,N'-bis(2-hydroxyethyl)pyrazine-2,5-dicarboxamide,
N,N'-bis(2-hydroxyethyl)pyrazine-2,6-dicarboxamide,
N-methyl-N-(2-hydroxyethyl-N'-methyl-N'(2-hydroxyethyl)pyrazine-2,5-dicarboxamide,
N-methyl-N-(2-hydroxyethyl)-N'-methyl-N'(2-hydroxyethyl)pyrazine-2,6-dicarboxamide,
N,N,N',N'-tetrakis(2-hydroxyethyl)pyrazine-2,5-dicarboxamide,
N,N,N',N'-tetrakis(2-hydroxyethyl)pyrazine-2,6-dicarboxamide,
N,N'-bis(2,3-dihydroxy-1-propyl)pyrazine-2,5-dicarboxamide,
N,N'-bis(2,3-dihydroxy-1-propyl)pyrazine-2,6-dicarboxamide,
N-methyl-N-(2,3-dihydroxy-1-propyl)-N'-methyl-N'-(2,3-dihydroxy-1-propyl)pyrazine-2,5-dicarboxamide,
N-methyl-N-(2,3-dihydroxy-1-propyl)-N'-methyl-N'-(2,3-dihydroxy-1-propyl)pyrazine-2,6-dicarboxamide,
N,N,N',N'-tetrakis(2,3-dihydroxy-1-propyl)pyrazine-2,5-dicarboxamide,
N,N,N',N'-tetrakis(2,3-dihydroxy-1-propyl)pyrazine-2,6-dicarboxamide,
N,N'-bis(1,3-dihydroxy-2-propyl)pyrazine-2,5-dicarboxamide,
N,N'-bis(1,3-dihydroxy-2-propyl)pyrazine-2,6-dicarboxamide,
N-methyl-N-(1,3-dihydroxy-2-propyl)-N'-methyl-N'-(1,3-dihydroxy-2-propyl)pyrazine-2,5-dicarboxamide,
N-methyl-N-(1,3-dihydroxy-2-propyl)-N'-methyl-N'-(1,3-dihydroxy-2-propyl)pyrazine-2,6-dicarboxamide,
N,N,N',N'-tetrakis(1,3-dihydroxy-2-propyl)pyrazine-2,5-dicarboxamide,
N,N,N',N'-tetrakis(1,3-dihydroxy-2-propyl)pyrazine-2,6-dicarboxamide,
N,N'-bis(2,3,4-trihydroxy-1-butyl)pyrazine-2,5-dicarboxamide,
N,N'-bis(2,3,4-trihydroxy-1-butyl)pyrazine-2,6-dicarboxamide,
N-methyl-N-(2,3,4-trihydroxy-1-butyl)-N'-methyl-N'-(2,3,4-trihydroxy-1-butyl)pyrazine-2,5-dicarboxamide,
N-methyl-N-(2,3,4-trihydroxy-1-butyl)-N'-methyl-N'-(2,3,4-trihydroxy-1-butyl)pyrazine-2,6-dicarboxamide,
N,N'-bis(1,3,4-trihydroxy-2-butyl)pyrazine-2,5-dicarboxamide,
N,N'-bis(1,3,4-trihydroxy-2-butyl)pyrazine-2,6-dicarboxamide,
N-methyl-N-(1,3,4-trihydroxy-2-butyl)-N'-methyl-N'-(1,3,4-trihydroxy-2-butyl)pyrazine-2,5-dicarboxamide,
N-methyl-N-(1,3,4-trihydroxy-2-butyl)-N'-methyl-N'-(1,3,4-trihydroxy-2-butyl)pyrazine-2,6-dicarboxamide,
N,N'-bis[2-(hydroxymethyl)-3-hydroxy-1-propyl]-pyrazine-2,5-dicarboxamide,
N,N'-bis[2-(hydroxymethyl)-3-hydroxy-1-propyl]-pyrazine-2,6-dicarboxamide, N-methyl-N-[2-(hydroxymethyl)-3-hydroxy-1-propyl]-N'-methyl-N'-[2-(hydroxymethyl)-3-hydroxy-1-propyl]-pyrazine-2,5-dicarboxamide,
N-methyl-N-[2-(hydroxymethyl)-3-hydroxy-1-propyl]-N'-methyl-N'-[2-(hydroxymethyl)-3-hydroxy-1-propyl]-pyrazine-2,6-dicarboxamide,
N,N,N',N'-tetrakis[2-(hydroxymethyl)-3-hydroxy-1-propyl]pyrazine-2,5-dicarboxamide,
N,N,N',N'-tetrakis[2-(hydroxymethyl)-3-hydroxy-1-propyl]pyrazine-2,6-dicarboxamide,
N,N'-bis[1,1,1-tri(hydroxymethyl)methyl]pyrazine-2,5-dicarboxamide,
N,N'-bis[1,1,1-tri(hydroxymethyl)methyl]pyrazine-2,6-dicarboxamide,
N-methyl-N-[1,1,1-tri(hydroxymethyl)methyl]-N'-methyl-N'-[1,1,1-tri(hydroxymethyl)methyl]pyrazine-2,5-dicarboxamide,
N-methyl-N-[1,1,1-tri(hydroxymethyl)methyl]-N'-methyl-N'-[1,1,1-tri(hydroxymethyl)methyl]pyrazine-2,6-dicarboxamide,
N,N'-bis[1,1-di(hydroxymethyl)-1-ethyl]pyrazine-2,5-dicarboxamide,
N,N'-bis[1,1-di(hydroxymethyl)-1-ethyl]pyrazine-2,6-dicarboxamide,
N-methyl-N-[1,1-di(hydroxymethyl)-1-ethyl]-N'-methyl-N'-[1,1-di(hydroxymethyl)-1-ethyl]pyrazine-2,5-dicarboxamide,
N-methyl-N-[1,1-di(hydroxymethyl)-1-ethyl]-N'-methyl-N'-[1,1-di(hydroxymethyl)-1-ethyl]pyrazine-2,6-dicarboxamide,
N,N'-bis(2-hydroxyethyl)pyridine-2,5-dicarboxamide,
N,N'-bis(2-hydroxyethyl)pyridine-2,6-dicarboxamide,
N,N'-bis(2-hydroxyethyl)pyridine-3,5-dicarboxamide,
N-methyl-N-(2-hydroxyethyl)-N'-methyl-N'-(2-hydroxyethyl)pyridine-2,5-dicarboxamide,
N-methyl-N-(2-hydroxyethyl)-N'-methyl-N'-(2-hydroxyethyl)pyridine-2,6-dicarboxamide,
N-methyl-N-(2-hydroxyethyl)-N'-methyl-N'-(2-hydroxyethyl)pyridine-3,5-dicarboxamide,
N,N,N',N'-tetrakis(2-hydroxyethyl)pyridine-2,5-dicarboxamide,
N,N,N',N'-tetrakis(2-hydroxyethyl)pyridine-2,6-dicarboxamide,
N,N,N',N'-tetrakis(2-hydroxyethyl)pyridine-3,5-dicarboxamide,
N,N'-bis(2,3-dihydroxy-1-propyl)pyridine-2,5-dicarboxamide,
N,N'-bis(2,3-dihydroxy-1-propyl)pyridine-2,6-dicarboxamide,
N,N'-bis(2,3-dihydroxy-1-propyl)pyridine-3,5-dicarboxamide,
N-methyl-N-(2,3-dihydroxy-1-propyl)-N'-methyl-N'-(2,3-dihydroxy-1-propyl)pyridine-2,5-dicarboxamide,
N-methyl-N-(2,3-dihydroxy-1-propyl)-N'-methyl-N'-(2,3-dihydroxy-1-propyl)pyridine-2,6-dicarboxamide,
N-methyl-N-(2,3-dihydroxy-1-propyl)-N'-methyl-N'-(2,3-dihydroxy-1-propyl)pyridine-3,5-dicarboxamide,
N,N,N',N'-tetrakis(2,3-dihydroxy-1-propyl)pyridine-2,5-dicarboxamide,
N,N,N',N'-tetrakis(2,3-dihydroxy-1-propyl)pyridine-2,6-dicarboxamide,
N,N,N',N'-tetrakis(2,3-dihydroxy-1-propyl)pyridine-3,5-dicarboxamide,
N,N'-bis(1,3-dihydroxy-2-propyl)pyridine-2,5-dicarboxamide,
N,N'-bis(1,3-dihydroxy-2-propyl)pyridine-2,6-dicarboxamide,
N,N'-bis(1,3-dihydroxy-2-propyl)pyridine-3,5-dicarboxamide,
N-methyl-N-(1,3-dihydroxy-2-propyl)-N'-methyl-N'-(1,3-dihydroxy-2-propyl)pyridine-2,5-dicarboxamide,
N-methyl-N-(1,3-dihydroxy-2-propyl)-N'-methyl-N'-(1,3-dihydroxy-2-propyl)pyridine-2,6-dicarboxamide,
N-methyl-N-(1,3-dihydroxy-2-propyl)-N'-methyl-N'-(1,3-dihydroxy-2-propyl)pyridine-3,5-dicarboxamide,
N,N,N',N'-tetrakis(1,3-dihydroxy-2-propyl)pyrazine-2,5-dicarboxamide,
N,N,N',N'-tetrakis(1,3-dihydroxy-2-propyl)pyrazine-2,6-dicarboxamide,
N,N'-bis(2,3,4-trihydroxy-1-butyl)pyridine-2,5-dicarboxamide,
N,N'-bis(2,3,4-trihydroxy-1-butyl)pyridine-2,6-dicarboxamide,
N,N'-bis(2,3,4-trihydroxy-1-butyl)pyridine-3,5-dicarboxamide,
N-methyl-N-(2,3,4-trihydroxy-1-butyl)-N'-methyl-N'-(2,3,4-trihydroxy-1-butyl)pyridine-2,5-dicarboxamide,
N-methyl-N-(2,3,4-trihydroxy-1-butyl)-N'-methyl-N'-(3,4-trihydroxy-1-butyl)pyridine-2,6-dicarboxamide,
N-methyl-N-(2,3,4-trihydroxy-1-butyl)-N'-methyl-N'-(2,3,4-trihydroxy-1-butyl)pyridine-3,5-dicarboxamide,
N,N'-bis(1,3,4-trihydroxy-2-butyl)pyridine-2,5-dicarboxamide,
N,N'-bis(1,3,4-trihydroxy-2-butyl)pyridine-2,6-dicarboxamide,
N,N'-bis(1,3,4-trihydroxy-2-butyl)pyridine-3,5-dicarboxamide,
N-methyl-N-(1,3,4-trihydroxy-2-butyl)-N'-methyl-N'-(1,3,4-trihydroxy-2-butyl)pyridine-2,5-dicarboxamide,
N-methyl-N-(1,3,4-trihydroxy-2-butyl)-N'-methyl-N'-(1,3,4-trihydroxy-2-butyl)pyridine-2,6-dicarboxamide,
N-methyl-N-(1,3,4-trihydroxy-2-butyl)-N'-methyl-N'-(1,3,4-trihydroxy-2-butyl)pyridine-3,5-dicarboxamide,
N,N'-bis[2-(hydroxymethyl)-3-hydroxy-1-propyl]-pyridine-2,5-dicarboxamide,
N,N'-bis[2-(hydroxyymethyl)-3-hydroxy-1-propyl]-pyridine-2,6-dicarboxamide,
N,N'-bis[2-(hydroxymethyl)-3-hydroxy-1-propyl]-pyridine-3,5-dicarboxamide,
N-methyl-N-[2-(hydroxymethyl)-3-hydroxy-1-propyl]-N'-methyl-N'-[2-(hydroxymethyl)-3-hydroxy-1-propyl]-pyridine-2,5-dicarboxamide,
N-methyl-N-[2-(hydroxymethyl)-3-hydroxy-1-propyl]-N'-methyl-N'-[2-(hydroxymethyl)-3-hydroxy-1-propyl]-pyridine-2,6-dicarboxamide,
N-methyl-N-[2-(hydroxymethyl)-3-hydroxy-1-propyl]-N'-methyl-N'-[2-(hydroxymethyl)-3-hydroxy-1-propyl]-pyridine-3,5-dicarboxamide,
N,N,N',N'-tetrakis[2-(hydroxymethyl)-3-hydroxy-1-propyl]pyridine-2,5-dicarboxamide,
N,N,N',N'-tetrakis[2-(hydroxymethyl)-3-hydroxy-1-propyl]pyridine-2,6-dicarboxamide,
N,N,N',N'-tetrakis[2-(hydroxymethyl)-3-hydroxy-1-propyl]pyridine-3,5-dicarboxamide,
N,N'-bis[1,1,1-tri(hydroxymethyl)methyl]pyridine-2,5-dicarboxamide,
N,N'-bis[1,1,1-tri(hydroxymethyl)methyl]pyridine-2,6-dicarboxamide,
N,N'-bis[1,1,1-tri(hydroxymethyl)methyl]pyridine-3,5-dicarboxamide,
N-methyl-N-[1,1,1-tri(hydroxymethyl)methyl]-N'-methyl-N'-[1,1,1-tri(hydroxymethyl)methyl]pyridine-2,5-dicarboxamide,
N-methyl-N-[1,1,1-tri(hydroxymethyl)methyl]-N'-methyl-N'-[1,1,1-tri(hydroxymethyl)methyl]pyridine-2,6-dicarboxamide, N-methyl-N-[1,1,1-tri(hydroxymethyl)methyl]-N'-methyl-N'-[1,1,1-tri(hydroxymethyl)methyl]pyridine-3,5-dicarboxamide,
N,N'-bis[1,1-di(hydroxymethyl)-1-ethyl]pyridine-2,5-dicarboxamide,
N,N'-bis[1,1-di(hydroxymethyl)-1-ethyl]pyridine-2,6-dicarboxamide,
N,N'-bis[1,1-di(hydroxymethyl)-1-ethyl]pyridine-3,5-dicarboxamide,
N-methyl-N-[1,1-di(hydroxymethyl)-1-ethyl]-N'-methyl-N'-[1,1-di(hydroxymethyl)-1-ethyl]pyridine-2,5-dicarboxamide,
N-methyl-N-[1,1-di(hydroxymethyl)-1-ethyl]-N'-methyl-N'-[1,1-di(hydroxymethyl)-1-ethyl]pyridine-2,6-dicarboxamide,
N-methyl-N-[1,1-di(hydroxymethyl)-1-ethyl]-N'-methyl-N'-[1,1-di(hydroxymethyl)-1-ethyl]pyridine-3,5-dicarboxamide,
N,N'-bis(2-hydroxyethyl)pyrazine-2,5-dimethanamine,
N,N'-bis(2-hydroxyethyl)pyrazine-2,6-dimethanamine,
N-methyl-N-(2-hydroxyethyl)-N'-methyl-N'-(2-hydroxyethyl)pyrazine-2,5-dimethanamine,
N-methyl-N-(2-hydroxyethyl)-N'-methyl-N'-(2-hydroxyethyl)pyrazine-2,6-dimethanamine,
N,N,N',N'-tetrakis(2-hydroxyethyl)pyrazine-2,5-dimethanamine,
N,N,N',N'-tetrakis(2-hydroxyethyl)pyrazine-2,6-dimethanamine,
N,N'-bis(2,3-dihydroxy-1-propyl)pyrazine-2,5-dimethanamine,
N,N'-bis(2,3-dihydroxy-1-propyl)pyrazine-2,6-dimethanamine,
N-methyl-N-(2,3-dihydroxy-1-propyl)-N'-methyl-N'-(2,3-dihydroxy-1-propyl)pyrazine-2,5-dimethanamine,
N-methyl-N-(2,3-dihydroxy-1-propyl)-N'-methyl-N'-(2,3-dihydroxy-1-propyl)pyrazine-2,6-dimethanamine,
N,N,N',N'-tetrakis(2,3-dihydroxy-1-propyl)pyrazine-2,5-dimethanamine,
N,N,N',N'-tetrakis(2,3-dihydroxy-1-propyl)pyrazine-2,6-dimethanamine,
N,N'-bis(1,3-dihydroxy-2-propyl)pyrazine-2,5-dimethanamine,
N,N'-bis(1,3-dihydroxy-2-propyl)pyrazine-2,6-dimethanamine,
N-methyl-N-(1,3-dihydroxy-2-propyl)-N'-methyl-N'-(1,3-dihydroxy-2-propyl)pyrazine-2,5-dimethanamine,
N-methyl-N-(1,3-dihydroxy-2-propyl)-N'-methyl-N'-(1,3-dihydroxy-2-propyl)pyrazine-2,6-dimethanamine,
N,N,N',N'-tetrakis(1,3-dihydroxy-2-propyl)pyrazine-2,5-dimethanamine,
N,N,N',N'-tetrakis(1,3-dihydroxy-2-propyl)pyrazine-2,6-dimethanamine,
N,N'-bis(2,3,4-trihydroxy-1-butyl)pyrazine-2,5-dimethanamine,
N,N'-bis(2,3,4-trihydroxy-1-butyl)pyrazine-2,6-dimethanamine,
N-methyl-N-(2,3,4-trihydroxy-1-butyl)-N'-methyl-N'-(2,3,4-trihydroxy-1-butyl)pyrazine-2,5-dimethanamine,
N-methyl-N-(2,3,4-trihydroxy-1-butyl)-N'-methyl-N'-(2,3,4-trihydroxy-1-butyl)pyrazine-2,6-dimethanamine,
N,N'-bis(1,3,4-trihydroxy-2-butyl)pyrazine-2,5-dimethanamine,
N,N'-bis(1,3,4-trihydroxy-2-butyl)pyrazine-2,6-dimethanamine,
N-methyl-N-(1,3,4-trihydroxy-2-butyl)-N'-methyl-N'-(1,3,4-trihydroxy-2-butyl)pyrazine-2,5-dimethanamine,
N-methyl-N-(1,3,4-trihydroxy-2-butyl)-N'-methyl-N'-(1,3,4-trihydroxy-2-butyl)pyrazine-2,6-dimethanamine,
N,N'-bis[2-(hydroxymethyl)-3-hydroxy-1-propyl]-pyrazine-2,5-dimethanamine,
N,N'-bis[2-(hydroxymethyl)-3-hydroxy-1-propyl]-pyrazine-2,6-dimethanamine,
N-methyl-N-[2-(hydroxymethyl)-3-hydroxy-1-propyl]-N'-methyl-N'[2-(hydroxymethyl)-3-hydroxy-1-propyl]-pyrazine-2,5-dimethanamine,
N-methyl-N-[2-(hydroxymethyl)-3-hydroxy-1-propyl]-N'-methyl-N'-[2-(hydroxymethyl)-3-hydroxy-1-propyl]-pyrazine-2,6-dimethanamine,
N,N,N',N'-tetrakis[2-(hydroxymethyl)-3-hydroxy-1-propyl]pyrazine-2,5-dimethanamine,
N,N,N',N'-tetrakis[2-(hydroxymethyl)-3-hydroxy-1-propyl]pyrazine-2,6-dimethanamine,
N,N'-bis[1,1,1-tri(hydroxymethyl)methyl]pyrazine-2,5-dimethanamine,
N,N'-bis[1,1,1-tri(hydroxymethyl)methyl]pyrazine-2,6-dimethanamine,
N-methyl-N-[1,1,1-tri(hydroxymethyl)methyl]-N'-methyl-N'-[1,1,1-tri(hydroxymethyl)methyl]pyrazine-2,5-dimethanamine,
N-methyl-N-[1,1,1-tri(hydroxymethyl)methyl]-N'-methyl-N'-[1,1,1tri(hydroxymethyl)methyl]pyrazine-2,6-dimethanamine,
N,N'-bis[1,1-di(hydroxymethyl)-1-ethyl]pyrazine-2,5-dimethanamine,
N,N'-bis[1,1-di(hydroxymethyl)-1-ethyl]pyrazine-2,6-dimethanamine,
N-methyl-N-[1,1-di(hydroxymethyl)-1-ethyl]-N'-methyl-N'-[1,1-di(hydroxymethyl)-1-ethyl]pyrazine-2,5-dimethanamine,
N-methyl-N-[1,1-di(hydroxymethyl)-1-ethyl]-N'-methyl-N'-[1,1-di(hydroxymethyl)-1-ethyl]pyrazine-2,6-dimethanamine,
N,N'-bis(2-hydroxyethyl)pyridine-2,5-dimethanamine,
N,N'-bis(2-hydroxyethyl)pyridine-2,6-dimethanamine,
N,N'-bis(2-hydroxyethyl)pyridine-3,5-dimethanamine,
N-methyl-N-(2-hydroxyethyl)-N'-methyl-N'-(2-hydroxyethyl)pyridine-2,5-dimethanamine,
N-methyl-N-(2-hydroxyethyl)-N'-methyl-N'-(2-hydroxyethyl)pyridine-2,6-dimethanamine,
N-methyl-N-(2-hydroxyethyl)-N'-methyl-N'-(2-hydroxyethyl)pyridine-3,5-dimethanamine,
N,N,N',N'-tetrakis(2-hydroxyethyl)pyridine-2,5-dimethanamine,
N,N,N',N'-tetrakis(2-hydroxyethyl)pyridine-2,6-dimethanamine,
N,N,N',N'-tetrakis(2-hydroxyethyl)pyridine-3,5-dimethanamine,
N,N'-bis(2,3-dihydroxy-1-propyl)pyridine-2,5-dimethanamine,
N,N'-bis(2,3-dihydroxy-1-propyl)pyridine-2,6-dimethanamine,
N,N'-bis(2,3-dihydroxy-1-propyl)pyridine-3,5-dimethanamine,
N-methyl-N-(2,3-dihydroxy-1-propyl)-N'-methyl-N'-(2,3-dihydroxy-1-propyl)pyridine-2,5-dimethanamine,
N-methyl-N-(2,3-dihydroxy-1-propyl)-N'-methyl-N'-(2,3-dihydroxy-1-propyl)pyridine-2,6-dimethanamine,
N-methyl-N-(2,3-dihydroxy-1-propyl)-N'-methyl-N'-(2,3-dihydroxy-1-propyl)pyridine-3,5-dimethanamine,
N,N,N',N'-tetrakis(2,3-dihydroxy-1-propyl)pyridine-2,5-dimethanamine,
N,N,N',N'-tetrakis(2,3-dihydroxy-1-propyl)pyridine-2,6-dimethanamine,
N,N,N',N'-tetrakis(2,3-dihydroxy-1-propyl)pyridine-3,5-dimethanamine, N,N'-bis(1,3-dihydroxy-2-propyl)pyridine-2,5-dimethanamine,
N,N'-bis(1,3-dihydroxy-2-propyl)pyridine-2,6-dimethanamine,
N,N'-bis(1,3-dihydroxy-2-propyl)pyridine-3,5-dimethanamine,
N-methyl-N-(1,3-dihydroxy-2-propyl)-N'-methyl-N'-(1,3-dihydroxy-2-propyl)pyridine-2,5-dimethanamine,
N-methyl-N-(1,3-dihydroxy-2-propyl)-N'-methyl-N'-(1,3-dihydroxy-2-propyl)pyridine-2,6-dimethanamine,
N-methyl-N-(1,3-dihydroxy-2-propyl)-N'-methyl-N'-(1,3-dihydroxy-2-propyl)pyridine-3,5-dimethanamine,
N,N,N',N'-tetrakis(1,3-dihydroxy-2-propyl)pyridine-2,5-dimethanamine,
N,N,N',N'-tetrakis(1,3-dihydroxy-2-propyl)pyridine-2,6-dimethanamine,
N,N,N',N'-tetrakis(1,3-dihydroxy-2-propyl)pyridine-3,5-dimethanamine,
N,N'-bis(2,3,4-trihydroxy-1-butyl)pyridine-2,5-dimethanamine,
N,N'-bis(2,3,4-trihydroxy-1-butyl)pyridine-2,6-dimethanamine,
N,N'-bis(2,3,4-trihydroxy-1-butyl)pyridine-3,5-dimethanamine,
N-methyl-N-(2,3,4-trihydroxy-1-butyl)-N'-methyl-N'-(2,3,4-trihydroxy-1-butyl)pyridine-2,5-dimethanamine,
N-methyl-N-(2,3,4-trihydroxy-1-butyl)-N'-methyl-N'-(2,3,4-trihydroxy-1-butyl)pyridine-2,6-dimethanamine,
N-methyl-N-(2,3,4-trihydroxy-1-butyl)-N'-methyl-N'-(2,3,4-trihydroxy-1-butyl)pyridine-3,5-dimethanamine,
N,N'-bis(1,3,4-trihydroxy-2-butyl)pyridine-2,5-dimethanamine,
N,N'-bis(1,3,4-trihydroxy-2-butyl)pyridine-2,6-dimethanamine,
N,N'-bis(1,3,4-trihydroxy-2-butyl)pyridine-3,5-dimethanamine,
N-methyl-N-(1,3,4-trihydroxy-2-butyl)-N'-methyl-N'-(1,3,4-trihydroxy-2-butyl)pyridine-2,5-dimethanamine,
N-methyl-N-(1,3,4-trihydroxy-2-butyl)-N'-methyl-N'-(1,3,4-trihydroxy-2-butyl)pyridine-2,6-dimethanamine,
N-methyl-N-(1,3,4-trihydroxy-2-butyl)-N'-methyl-N'-(1,3,4-trihydroxy-2-butyl)pyridine-3,5-dimethanamine,
N,N'-bis[2-(hydroxymethyl)-3-hydroxy-1-propyl]-pyridine-2,5-dimethanamine,
N,N'-bis[2-(hydroxymethyl)-3-hydroxy-1-propyl]-pyridine-2,6-dimethanamine,
N,N'-bis[2-(hydroxymethyl)-3-hydroxy-1-propyl]-pyridine-3,5-dimethanamine,
N-methyl-N-[2-(hydroxymethyl)-3-hydroxy-1-propyl]N'-methyl-N'-[2-(hydroxymethyl)-3-hydroxy-1-propyl]-pyridine-2,5-dimethanamine,
N-methyl-N-[2-(hydroxymethyl)-3-hydroxy-1-propyl]-N'-methyl-N'-[2-(hydroxymethyl)-3-hydroxy-1-propyl]-pyridine-2,6-dimethanamine,
N-methyl-N-[2-(hydroxymethyl)-3-hydroxy-1-propyl]-N'-methyl-N'-[2-(hydroxymethyl)-3-hydroxy-1-propyl]-pyridine-3,5-dimethanamine,
N,N,N',N'-tetrakis[2-(hydroxymethyl)-3-hydroxy-1-propyl]pyridine-2,5-dimethanamine,
N,N,N',N'-tetrakis[2-(hydroxymethyl)-3-hydroxy-1-propyl]pyridine-2,6-dimethanamine,
N,N,N',N'-tetrakis[2-(hydroxymethyl)-3-hydroxy-1-propyl]pyridine-3,5-dimethanamine,
N,N'-bis[1,1,1-tri(hydroxymethyl)methyl]pyridine-2,5-dimethanamine,
N,N'-bis[1,1,1-tri(hydroxymethyl)methyl]pyridine-2,6-dimethanamine,
N,N'-bis[1,1,1-tri(hydroxymethyl)methyl]pyridine-3,5-dimethanamine,
N-methyl-N-[1,1,1-tri(hydroxymethyl)methyl]-N'-methyl-N'-[1,1,1-tri(hydroxymethyl)methyl]pyridine-2,5-dimethanamine,
N-methyl-N-[1,1,1-tri(hydroxymethyl)methyl]-N'-methyl-N'-[1,1,1-tri(hydroxymethyl)methyl]pyridine-2,6-dimethanamine,
N-methyl-N-[1,1,1-tri(hydroxymethyl)methyl]-N'-methyl-N'-[1,1,1-tri(hydroxymethyl)methyl]pyridine-3,5-dimethanamine,
N,N'-bis[1,1-di(hydroxymethyl)-1-ethyl]pyridine-2,5-dimethanamine,
N,N'-bis[1,1-di(hydroxymethyl)-1-ethyl]pyridine-2,6-dimethanamine,
N,N'-bis[1,1-di(hydroxymethyl)-1-ethyl]pyridine-3,5-dimethanamine,
N-methyl-N-[1,1-di(hydroxymethyl)-1-ethyl]-N'-methyl-N'-[1,1-di(hydroxymethyl)-1-ethyl]pyridine-2,5-dimahanamine,
N-methyl-N-[1,1-di(hydroxymethyl)-1-ethyl]-N'-methyl-N'-[1,1-di(hydroxymethyl)-1-ethyl]pyridine-2,6-dimethanamine,
N-methyl-N-[1,1-di(hydroxymethyl)-1-ethyl]-N'-methyl-N'-[1,1-di(hydroxymethyl)-1-ethyl]pyridine-3,5-dimethanamine,
2,5-bis(2-hydroxyethyloxymethyl)pyrazine,
2,6-bis(2-hydroxyethyloxymethyl)pyrazine,
2,5-bis[(2R)-2,3-dihydroxy-1-propyloxymethyl]pyrazine,
2,5-bis[(2S)-2,3-dihydroxy-1-propyloxymethyl]pyrazine,
2,6-bis[(2R)-2,3-dihydroxy-1-propyloxymethyl]pyrazine,
2,6-bis[(2S)-2,3-dihydroxy-1-propyloxymethyl]pyrazine,
2,5-bis(1,3-dihydroxy-2-propyloxymethyl)pyrazine,
2,6-bis(1,3-dihydroxy-2-propyloxymethyl)pyrazine,
2,5-bis(2,3,4-trihydroxy-1-butyloxymethyl)pyrazine,
2,6-bis(2,3,4-trihydroxy-1-butyloxymethyl)pyrazine,
2,5-bis(1,3,4-trihydroxy-2-butyloxymethyl)pyrazine,
2,6-bis(1,3,4-trihydroxy-2-butyloxymethyl)pyrazine,
2,5-bis[2-(hydroxymethyl)-3-hydroxy-1-propyloxymethyl]pyrazine,
2,6-bis[2-(hydroxymethyl)-3-hydroxy-1-propyloxymethyl]pyrazine,
2,5-bis[1,1,1-tri(hydroxymethyl)methyloxymethyl]-pyrazine,
2,6-bis[1,1,1-tri(hydroxymethyl)methyloxymethyl]-pyrazine,
2,5-bis[1,1-di(hydroxymethyl)-1-ethyloxymethyl]-pyrazine,
2,6-bis[1,1-di(hydroxymethyl)-1-ethylbxymethyl]-pyrazine,
2,5-bis(2-hydroxyethyloxymethyl)pyridine,
2,6-bis(2-hydroxyethyloxymethyl)pyridine,
3,5-bis(2-hydroxyethyloxymethyl)pyridine,
2,5-bis(2,3-dihydroxy-1-propyloxymethyl)pyridine,
2,6-bis(2,3-dihydroxy-1-propyloxymethyl)pyridine,
3,5-bis(2,3-dihydroxy-1-propyloxymethyl)pyridine,
2,5-bis(1,3-dihydroxy-2-propyloxymethyl)pyridine,
2,6-bis(1,3-dihydroxy-2-propyloxymethyl)pyridine,
3,5-bis(1,3-dihydroxy-2-propyloxymethyl)pyridine,
2,5-bis(2,3,4-trihydroxy-1-butyloxymethyl)pyridine,
2,6-bis(2,3,4-trihydroxy-1-butyloxymethyl)pyridine,
3,5-bis(2,3,4-trihydroxy-1-butyloxymethyl)pyridine,
2,5-bis(1,3,4-trihydroxy-2-butyloxymethyl)pyridine,
2,6-bis(1,3,4-trihydroxy-2-butyloxymethyl)pyridine,
3,5-bis(1,3,4-trihydroxy-2-butyloxymethyl)pyridine,
2,5-bis[2-(hydroxymethyl)-3-hydroxy-1-propyloxymethyl]pyridine, 2,6-bis[2-(hydroxymethyl)-3-hydroxy-1-propyloxymethyl] pyridine,
3,5-bis[2-(hydroxymethyl)-3-hydroxy-1-propyloxymethyl] pyridine,
2,5-bis[1,1,1-tri(hydroxymethyl)methyloxymethyl]-pyridine,
2,6-bis[1,1,1-tri(hydroxymethyl)methyloxymethyl]-pyridine,
3,5-bis[1,1,1-tri(hydroxymethyl)methyloxymethyl]-pyridine,
2,5-bis[1,1-di(hydroxymethyl)-1-ethyloxymethyl]-pyridine,
2,6-bis[1,1-di(hydroxymethyl)-1-ethyloxymethyl]-pyridine,
3,5-bis[1,1-di(hydroxymethyl)-1-ethyloxymethyl]-pyridine,
bis-N,N'-(2-hydroxyethylamido)-2,5-pyrazine,
bis-N,N'-(2-hydroxyethylamido)-2,6-pyrazine,
bis[N-methyl-(2-hydroxyethylamido)]-2,5-pyrazine,
bis[N-methyl-(2-hydroxyethylamido)]-2,6-pyrazine,
bis(2,3-dihydroxy-1-propylamido)-2,5-pyrazine,
bis(2,3-dihydroxy-1-propylamido)-2,6-pyrazine,
bis[N-methyl-(2,3-dihydroxy-1-propylamido)]-2,5-pyrazine,
bis[N-methyl-(2,3-dihydroxy-1-propylamido)]-2,6-pyrazine,
bis[N-methyl-(1,3-dihydroxy-2-propylamido)]-2,5-pyrazine,
bis[N-methyl-(1,3-dihydroxy-2-propylamido)]-2,6-pyrazine,
bis(2,3,4-trihydroxy-1-butylamido)-2,5-pyrazine,
bis(2,3,4-trihydroxy-1-butylamido)-2,6-pyrazine,
bis[N-methyl-(2,3,4-trihydroxy-1-butylamido)]-2,5-pyrazine,
bis[N-methyl-(2,3,4-trihydroxy-1-butylamido)]-2,6-pyrazine,
bis(1,3,4-trihydroxy-2-butylamido)-2,5-pyrazine,
bis(1,3,4-trihydroxy-2-butylamido)-2,6-pyrazine,
bis[N-methyl-(1,3,4-trihydroxy-2-butylamido)]-2,5-pyrazine,
bis[N-methyl-(1,3,4-trihydroxy-2-butylamido)]-2,6-pyrazine,
bis[2-(hydroxymethyl)-3-hydroxy-1-propylamido]-2,5-pyrazine,
bis[2-(hydroxymethyl)-3-hydroxy-1-propylamido]-2,6-pyrazine,
bis{[N-methyl-[2-(hydroxymethyl)-3-hydroxy-1-propylamido]}-2,5-pyrazine,
bis{[N-methyl-[2-(hydroxymethyl)-3-hydroxy-1-propylamido]}-2,6-pyrazine,
bis[1,1,1-tri(hydroxymethyl)methylamido]-2,5-pyrazine,
bis[1,1,1-tri(hydroxymethyl)methylamido]-2,6-pyrazine,
bis{[N-methyl-[1,1,1-tri(hydroxymethyl)methylamido]}-2,5-pyrazine,
bis{[N-methyl-[1,1,1-tri(hydroxymethyl)methylamido]}-2,6-pyrazine,
bis[1,1-di(hydroxymethyl)-1-ethylamido]-2,5-pyrazine,
bis[1,1-di(hydroxymethyl)-1-ethylamido]-2,6-pyrazine,
bis{[N-methyl-[1,1-di(hydroxymethyl)-1-ethylamido]}-2,5-pyrazine,
bis{[N-methyl-[1,1-di(hydroxymethyl)-1-ethylamido]}-2,6-pyrazine,
bis[N,N'-(2-hydroxyethylamido)]-2,5-pyridine,
bis[N,N'-(2-hydroxyethylamido)]-2,6-pyridine,
bis[N,N'-(2-hydroxyethylamido)]-3,5-pyridine,
bis[N-methyl-(2-hydroxyethylamido)]-2,5-pyridine,
bis[N-methyl-(2-hydroxyethylamido)]-2,6-pyridine,
bis[N-methyl-(2-hydroxyethylamido)]-3,5-pyridine,
bis(2,3-dihydroxy-1-propylamido)-2,5-pyridine,
bis(2,3-dihydroxy-1-propylamido)-2,6-pyridine,
bis(2,3-dihydroxy-1-propylamido)-3,5-pyridine,
bis[N-methyl-(2,3-dihydroxy-1-propylamido)]-2,5-pyridine,
bis[N-methyl-(2,3-dihydroxy-1-propylamido)]-2,6-pyridine,
bis[N-methyl-(2,3-dihydroxy-1-propylamido)]-3,5-pyridine,
bis[N-methyl-(1,3-dihydroxy-2-propylamido)]-2,5-pyridine,
bis[N-methyl-(1,3-dihydroxy-2-propylamido)]-2,6-pyridine,
bis[N-methyl-(1,3-dihydroxy-2-propylamido)]-3,5-pyridine,
bis(2,3,4-trihydroxy-1-butylamido)-2,5-pyridine,
bis(2,3,4-trihydroxy-1-butylamido)-2,6-pyridine,
bis(2,3,4-trihydroxy-1-butylamido)-3,5-pyridine,
bis[N-methyl-(2,3,4-trihydroxy-1-butylamido)]-2,5-pyridine,
bis[N-methyl-(2,3,4-trihydroxy-1-butylamido)]-2,6-pyridine,
bis[N-methyl(2,3,4-trihydroxy-1-butylamido)]-3,5-pyrirdine,
bis(1,3,4-trihydroxy-2-butylamido)-2,5-pyridine,
bis(1,3,4-trihydroxy-2-butylamido)-2,6-pyridine,
bis(1,3,4-trihydroxy-2-butylamido)-3,5-pyridine,
bis[N-methyl-(1,3,4-trihydroxy-2-butylamido)]-2,5-pyridine,
bis[N-methyl-(1,3,4-trihydroxy-2-butylamido)]-2,6-pyridine,
bis[N-methyl-(1,3,4-trihydroxy-2-butylamido)]-3,5-pyridine,
bis[2-(hydroxymethyl)-3-hydroxy-1-propylamido]-2,5-pyridine,
bis[2-(hydroxymethyl)-3-hydroxy-1-propylamido]-2,6-pyridine,
bis[2-(hydroxymethyl)-3-hydroxy-1-propylamido]-3,5-pyridine,
bis{[N-methyl-[2-(hydroxymethyl)-3-hydroxy-1-propylamido]}-2,5-pyridine,
bis{[N-methyl-[2-(hydroxymethyl)-3-hydroxy-1-propylamido]}-2,6-pyridine,
bis{[N-methyl-[2-(hydroxymethyl)-3-hydroxy-1-propylamido]}-3,5-pyridine,
bis[1,1,1-tri(hydroxymethyl)methylamido]-2,5-pyridine,
bis[1,1,1-tri(hydroxymethyl)methylamido]-2,6-pyridine,
bis[1,1,1-tri(hydroxymethyl)methylamido]-3,5-pyridine,
bis{[N-methyl-[1,1,1-tri(hydroxymethyl)methylamido]}-2,5-pyridine,
bis{[N-methyl-[1,1,1-tri(hydroxymethyl)methylamido]}-2,6-pyridine,
bis{[N-methyl-[1,1,1-tri(hydroxymethyl)methylamido]}-3,5-pyridine,
bis[1,1-di(hydroxymethyl)-1-ethylamido]-2,5-pyridine,
bis[1,1-di(hydroxymethyl)-1-ethylamido]-2,6-pyridine,
bis[1,1-di(hydroxymethyl)-1-ethylamido]-3,5-pyridine,
bis{[N-methyl-[1,1-di(hydroxymethyl)-1-ethylamido]}-2,5-pyridine,
bis{[N-methyl-[1,1-di(hydroxymethyl)-1-ethylamido]}-2,6-pyridine,
bis{[N-methyl-[1,1-di(hydroxymethyl)-1-ethylamido]}-3,5-pyridine, or a stereoisomer of these compounds or a salt of such a compound with a pharmaceutically acceptable inorganic or organic acid.

The medicaments which are particularly preferred are those which contain a compound of formula (I) in which either R represents a nitrogen atom, $R_1$ represents a radical —CO—$NR_5R_6$, —CO—N($CH_2$—(CHOH)$_n$—$CH_2OH$)$_2$ in which n is equal to 0, 1, 2, 3 or 4, —$CH_2$—$NR_5R_6$, —$CH_2$—N($CH_2$—(CHOH)$_y$—$CH_2OH$)$_2$ in which y is equal to 0, 1, 2, 3 or 4, and one of the substituents $R_3$ or $R_4$ represents a hydrogen atom and the other is identical to $R_1$, $R_2$ represents a hydrogen atom, $R_5$ represents a hydrogen atom or an alkyl radical and $R_6$ represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$ or —C($CH_2OH$)$_3$, or R represents a CH residue, $R_1$ and $R_4$ are identical and each represent a radical —CO—$NR_5R_6$, $R_2$ and $R_3$ each represent a hydrogen atom, $R_5$ represents a hydrogen atom or an alkyl radical and $R_6$ represents a —CH($CH_2OH$)$_2$ radical, or R represents a CH residue, $R_1$ and $R_3$ are identical and each represent a radical —$NR_5$—CO—$R_6$, $R_2$ and $R_4$ each represent a hydrogen atom, $R_5$ represents a hydrogen atom or an alkyl radical and $R_6$ represents a radical -alk-O-alk, or R represents a CH residue, $R_2$ and $R_3$ are identical and each represent a radical —CO—$NR_5R_6$, —$CH_2$—O—$R_6$, —$NR_5$—CO—$R_6$, —$CH_2$—$NR_5R_6$, $R_1$ and $R_4$ each represent a hydrogen atom, $R_5$ represents a hydrogen atom or an alkyl radical and $R_6$ represents a radical -alk-O-alk, —CH($CH_2OH$)$_2$, —C($CH_2OH$)$_3$, —C($CH_3$)($CH_2OH$)$_2$, alk represents an alkyl radical, their stereoisomers and their salts with a pharmaceutically acceptable inorganic or organic acid.

The medicaments even more particularly preferred are those which contain, as active principle, a compound of formula (I) chosen from the following compounds:

N,N'-bis[(tris(hydroxymethyl)methyl]pyrazine-2,5-dicarboxamide,
N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dicarboxamide,
N,N'-bis(1,3-dihydroxy-2-propyl)pyrazine-2,5-dicarboxamide,
N,N'-bis(2,3-dihydroxy-1-propyl)pyrazine-2,5-dicarboxamide,
N,N,N',N'-tetrakis(2-hydroxyethyl)pyrazine-2,5-dicarboxamide,
bis{N-[2(R,S)-3-dihydroxy-1-propyl]-N-methyl}pyrazine-2,5-dicarboxamide,
N,N'-bis(2-methoxyethyl)pyrazine-2,5-dicarboxamide,
N,N'-bis(2-hydroxyethyloxyethyl)pyrazine-2,5-dicarboxamide,
N,N'-bis(1,3-dihydroxy-2-propyl)pyridine-2,6-dicarboxamide,
N,N'-bis(1,3-dihydroxy-2-methyl-2-propyl)pyridine-2,6-dicarboxamide,
N,N'-bis(1,3-dihydroxy-2-propyl)pyridine-3,5-dicarboxamide,
N,N'-bis(1,3-dihydroxy-2-propyl)pyrazine-2,5-dimethanamine,
N,N,N',N'-tetrakis(2-hydroxyethyl)pyrazine-2,5-dimethanamine,
N,N'-bis(1,3-dihydroxy-2-propyl)pyrazine-2,5-dimethanamine,
N,N'-(1,3-dihydroxy-2-methyl-2-propyl)pyridine-2,6-dimethanamine,
N,N'-(1,3-dihydroxy-2-propyl)pyridine-2,6-dimethanamine,
2,5-bis[N,N'-(3-methoxy-1-propylamido)]pyridine,
2,6-bis(2-methoxyethyloxymethyl)pyridine,
N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dimethanamine,
2,6-bis[N,N'-(1,3-dihydroxy-2-methyl-2-propylamido)]-pyridine-2,6-bis[N,N'-(1,3-dihydroxy-2-methyl-2-propylamido)]pyridine or a salt of such a compound with a pharmaceutically acceptable inorganic or organic acid.

The compounds of formula (I) for which $R_1$ and $R_4$ each represent a hydrogen atom and either (a) R represents a CH residue, $R_2$ and $R_3$ are identical and each represent a radical —CO—$NR_5R_6$ for which $R_5$ represents a hydrogen atom and $R_6$ represents a radical —$CH_2$—(CHOH)m—$CH_2OH$ in which m is equal to 0, or alternatively $R_5$ represents an alkyl radical containing one carbon atom and $R_6$ represents a radical —$CH_2$—(CHOH)m—$CH_2OH$ in which m is equal to 0, or (b) R represents a CH residue, $R_2$ and $R_3$ are identical and each represent a radical —$CH_2$—$NR_5R_6$ for which $R_5$ represents a hydrogen atom and $R_6$ represents a radical —$CH_2$—(CHOH)m—$CH_2OH$ in which m is equal to 4, or (c) R represents a CH residue, $R_2$ and $R_3$ are identical and each represent a radical —$CH_2$—$NR_5R_6$ for which $R_5$ represents an alkyl radical containing one carbon atom and $R_6$ represents a radical —$CH_2$—(CHOH)m—$CH_2OH$ in which m is equal to 0, or (d) R represents a CH residue, $R_2$ and $R_3$ are identical and each represent a radical —$CH_2$—$OR_6$ for which $R_6$ represents a radical —$CH_2$—(CHOH)m—$CH_2OH$ in which m is equal to 0, are described but no pharmacological activity is mentioned for them (J. Rammo et al., Liebigs Ann., 11, 1757 (1995); I. O. Kady et al., Tetrahedron Letters, 36, 23, 4031 (1995); S. Kumar et al., Tetrahedron Letters, 37, 12, 2071 (1996); T. Izumi et al., Bull. Chem. Soc. Jpn., 61, 3565 (1988)).

The compound of formula (I) for which R represents a CH residue, $R_1$ and $R_2$ are identical and each represent a radical —CO—$NR_5R_6$ for which $R_5$ is a hydrogen atom, $R_6$ represents a radical —$CH_2$—(CHOH)m—$CH_2OH$ and n is equal to 0, and $R_2$ and $R_3$ each represent a hydrogen atom, is described in Japanese patent JP 63-8143.

No pharmacological activity is described for the known compounds.

The other compounds of formula (I) are novel and form part of the invention in their natural form.

The preferred compounds of formula (I) are those for which: either

R represents a nitrogen atom, $R_1$ represents a radical —CO—$NR_5R_6$, —CO—N($CH_2$—(CHOH)$_n$—$CH_2OH$)$_2$ in which n is equal to 0, 1, 2, 3 or 4, —$CH_2$—$NR_5R_6$, —$CH_2$—N($CH_2$—(CHOH)$_y$—$CH_2OH$)$_2$ in which y is equal to 0, 1, 2, 3 or 4, and one of the substituents $R_3$ or $R_4$ represents a hydrogen atom and the other is identical to $R_1$, $R_2$ represents a hydrogen atom, $R_5$ represents a hydrogen atom or an alkyl radical and $R_6$ represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$ or —C($CH_2OH$)$_3$, or R represents a CH residue, $R_1$ and $R_4$ are identical and each represent a radical —CO—$NR_5R_6$, $R_2$ and $R_3$ each represent a hydrogen atom, $R_5$ represents a hydrogen atom or an alkyl radical and $R_6$ represents a —CH($CH_2OH$)$_2$ radical, or R represents a CH residue, $R_1$ and $R_3$ are identical and each represent a radical —$NR_5$—CO—$R_6$, $R_2$ and $R_4$ each represent a hydrogen atom, $R_5$ represents a hydrogen atom or an alkyl radical and $R_6$ represents a radical -alk-O-alk, or R represents a CH residue, $R_2$ and $R_3$ are identical and each represent a radical —CO—$NR_5R_6$, —$CH_2$—O—$R_6$, —$NR_5$—CO—$R_6$, —$CH_2$—$NR_5R_6$, $R_1$ and $R_4$ each represent a hydrogen atom, $R_5$ represents a hydrogen atom or an alkyl radical and $R_6$ represents a radical -alk-O-alk, —$CH(CH_2OH)_2$, —$C(CH_2OH)_3$, —$C(CH_3)(CH_2OH)_2$, alk represents an alkyl radical their stereoisomers and their salts with a pharmaceutically acceptable inorganic or organic acid.

The compounds of formula (I) which are even more particularly preferred are the following compounds:

N,N'-bis[(tris(hydroxymethyl)methyl]pyrazine-2,5-dicarboxamide

N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dicarboxamide N,N'-bis(1,3-dihydroxy-2-propyl)pyrazine-2,5-dicarboxamide N,N'-bis(2,3-dihydroxy-1-propyl)pyrazine-2,5-dicarboxamide N,N,N',N'-tetrakis(2-hydroxyethyl)pyrazine-2,5-dicarboxamide bis{N-[2(R,S)-3-dihydroxy-1-propyl]-N-methyl}pyrazine-2,5-dicarboxamide N,N'-bis(2-methoxyethyl)pyrazine-2,5-dicarboxamide N,N'-bis(2-hydroxyethyloxyethyl)pyrazine-2,5-dicarboxamide N,N'-bis(1,3-dihydroxy-2-propyl)pyridine-2,6-dicarboxamide N,N'-bis(1,3-dihydroxy-2-methyl-2-propyl)pyridine-2,6-dicarboxamide N,N'-bis(1,3-dihydroxy-2-propyl)pyridine-3,5-dicarboxamide N,N'-bis(1,3-dihydroxy-2-propyl)pyrazine-2,5-dimethanamine N,N,N',N'-tetrakis(2-hydroxyethyl)pyrazine-2,5-dimethanamine N,N'-bis(1,3-dihydroxy-2-propyl)pyrazine-2,5-dimethanamine N,N'-(1,3-dihydroxy-2-methyl-2-propyl)pyridine-2,6-dimethanamine N,N'-(1,3-dihydroxy-2-propyl)pyridine-2,6-dimethanamine 2,5-bis[N,N'-(3-methoxy-1-propylamido)]pyridine 2,6-bis(2-methoxyethyloxymethyl)pyridine N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dimethanamine 2,6-bis[N,N'-(1,3-dihydroxy-2-methyl-2-propylamido)]-pyridine-2,6-bis[N,N'-(1,3-dihydroxy-2-methyl-2-propylamido)]pyridine and their salts with an inorganic or organic acid.

The compounds of formula (I) for which R represents a nitrogen atom, $R_1$ represents a radical —CO—$NR_5R_6$, —CO—$N(CH(CH_2OH)_2)_2$, —CO—$N(CH_2OH)_2$, —CO—$N(CH_2—CH(CH_2OH)_2)_2$, —CO—$N(CH_2—(CHOH)_n—CH_2OH)_2$, and one of the substituents $R_3$ and $R_4$ represents a hydrogen atom and the other is identical to $R_1$ and $R_2$ represents a hydrogen atom, can be prepared by the action of a derivative of formula:

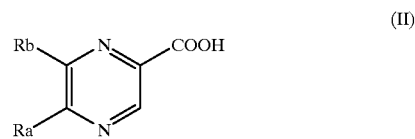

in which one of the substituents Ra or Rb represents a carboxyl radical and the other represents a hydrogen atom, or a reactive derivative of this diacid, on an amine HNRcRd (III) in which either Rc represents a hydrogen atom or an alkyl radical and Rd represents a radical —$CH_2$—(CHOH)$_m$—$CH_2OH$ in which m is equal to 0, 1, 2, 3 or 4, -alk-O-alk-$CH_2OH$, -alk-O-alk, —$CH(CH_2OH)_2$, —$C(CH_2OH)_3$, —$C(CH_3)(CH_2OH)_2$, —$CH_2$—CH$(CH_2OH)_2$ or —$CH(CH_2OH)(CHOH)_x$—$CH_2OH$ in which x is equal to 1, 2, 3 or 4 and alk represents an alkyl radical, or Rc and Rd are identical and each represent a radical —$CH_2$—(CHOH)$_n$—$CH_2OH$ in which n is equal to 0, 1, 2, 3 or 4, —$CH(CH_2OH)_2$, —$CH_2OH$ or —$CH_2$—CH$(CH_2OH)_2$.

When the diacid (II) is used, the process is performed in the presence of a coupling agent used in peptide chemistry, such as a carbodiimide (for example N,N'-dicyclohexylcarbodiimide) or N,N'-carbonyldiimidazole, in an inert solvent such as an ether (tetrahydrofuran or dioxane, for example), an amide (dimethylformamide) or a chlorinated solvent (methylene chloride, 1,2-dichloroethane or chloroform, for example) at a temperature of between 0° C. and the reflux temperature of the reaction mixture. When a diester is used, the process is then performed either in organic medium, optionally in the presence of an acid acceptor such as a nitrogenous organic base (trialkylamine, pyridine, 1,8-diazabicyclo[5.4.0]undec-7-ene or 1,5-diazabicyclo[4.3.0]non-5-ene, for example), in a solvent as mentioned above, or a mixture of these solvents, at a temperature of between 0° C. and the reflux temperature of the reaction mixture, or in a two-phase aqueous-organic medium in the presence of an alkali-metal or alkaline-earth metal base (sodium hydroxide or potassium hydroxide) or in the presence of an alkali-metal or alkaline-earth metal carbonate or bicarbonate, at a temperature of between 0 and 40° C.

The derivatives of formula (II) and their reactive derivatives are commercially available or can be obtained by application or adaptation of the methods described by W. J. Schut, H. I. X. Mager and W. Berends, Rec. Trav. Chim. Pays-Bas, 80, 391 (1961) and H. I. X. Mager and W. Berends, Rec. Trav. Chim. Pays-Bas, 77,827 (1958) or by oxidation of the corresponding dimethyl derivative, for example using selenium oxide, in a water-pyridine mixture, at a temperature of between 60 and 100° C. The diesters are obtained by esterification of the diacids, preferably using a lower ($C_{1-4}$) aliphatic alcohol, in the presence of an acid (preferably sulphuric acid), at the boiling point of the reaction medium.

The corresponding dimethyl derivatives are commercially available or can be obtained in particular by adaptation or application of the methods described in "The Pyrazines" G. B. Barlin, Chapter 4, pp. 68–77, in "The Chemistry of Heterocyclic Compounds", edited by A. Weissberger and E. C. Taylor—1982 —Interscience Publishers.

The amines of formula (III) are commercially available or can be obtained in particular by adaptation or application of the methods described in ouben-Weyl "Methoden der Organischen Chemie" Volume XI/1 pp. 1–1037—Georg Thieme Verlag—Stuttgart (1957).

The compounds of formula (I) for which either R represents a CH residue, $R_1$ and $R_4$ are identical and each represent a radical —CO—$NR_5R_6$, —CO—N(CH($CH_2OH$)$_2$)$_2$, —CO—N($CH_2OH$)$_2$, —CO—N($CH_2$—CH($CH_2OH$)$_2$)$_2$, —CO—N($CH_2$—(CHOH)$_n$—$CH_2OH$)$_2$, and $R_2$ and $R_3$ each represent a hydrogen atom, or R represents a CH residue, $R_1$ and $R_3$ are identical and each represent a radical —CO—$NR_5R_6$, —CO—N(CH($CH_2OH$)$_2$)$_2$, —CO—N($CH_2OH$)$_2$, —CO—N($CH_2$—CH($CH_2OH$)$_2$)$_2$, —CO—N($CH_2$—(CHOH)$_n$—$CH_2OH$)$_2$ and $R_2$ and $R_4$ each represent a hydrogen atom, or R represents a CH residue, $R_2$ and $R_3$ are identical and each represent a radical —CO—$NR_5R_6$, —CO—N(CH($CH_2OH$)$_2$)$_2$, —CO—N($CH_2OH$)$_2$, —CO—N($CH_2$—CH($CH_2OH$)$_2$)$_2$, —CO—N($CH_2$—(CHOH)$_n$—$CH_2OH$)$_2$ and $R_1$ and $R_4$ each represent a hydrogen atom, can be prepared by the action of a diacid of formula:

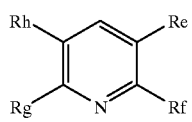

(IV)

in which either Re and Rh are identical and each represent a carboxyl radical and Rf and Rg each represent a hydrogen atom, or Re and Rg are identical and each represent a carboxyl radical and Rf and Rh each represent a hydrogen atom, or Rf and Rg are identical and each represent a carboxyl radical and Re and Rh each represent a hydrogen atom or a reactive derivative of this diacid, on an amine HNRcRd (III) in which either Rc represents a hydrogen atom or an alkyl radical and Rd represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$, —C($CH_2OH$)$_3$, —C($CH_3$) ($CH_2OH$)$_2$, —$CH_2$—CH($CH_2OH$)$_2$ or —CH($CH_2OH$) (CHOH)$_x$—$CH_2OH$ in which x is equal to 1, 2, 3 or 4 and alk represents an alkyl radical, or Rc and Rd are identical and each represent a radical —$CH_2$—(CHOH)$_n$—$CH_2OH$ in which n is equal to 0, 1, 2, 3 or 4, —CH($CH_2OH$)$_2$, —$CH_2OH$ or —$CH_2$—CH($CH_2OH$)$_2$.

This reaction is carried out under the conditions mentioned above for the reaction of (II) with (III).

The derivatives of formula (IV) are commercially available or can be obtained by application or adaptation of the methods described by H. Meyer, Mont. Chem., 24, 195 (1903) and Mont. Chem., 35, 781 (1914) or by oxidation of the corresponding dimethyl derivatives which are commercially available, for example using potassium permanganate at a temperature of between 20° C. and 100° C. The diesters are obtained by esterification of the diacids, preferably using a lower ($C_{1-4}$) aliphatic alcohol, in the presence of acid (preferably sulphuric acid), at the boiling point of the reaction medium.

The compounds of formula (I) for which R represents a nitrogen atom, $R_1$ represents a radical —$CH_2$—O—$R_6$ and one of the substituents $R_3$ or $R_4$ represents a hydrogen atom and the other is identical to $R_1$ and $R_2$ represents a hydrogen atom, can be prepared by the action of a derivative of formula:

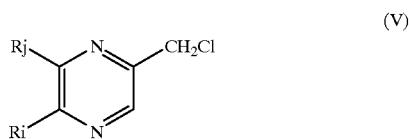

(V)

in which one of the substituents Ri or Rj represents a —$CH_2Cl$ radical and the other represents a hydrogen atom, on a derivative $R_6OH$ (VI) for which $R_6$ has the same meanings as in formula (I) and in which the hydroxyl functions are optionally protected in cyclic acetal form.

This reaction is generally carried out by the action of the alkali metal (preferably sodium or potassium) alkoxide corresponding to $R_6OH$, in an inert solvent such as an ether (for example tetrahydrofuran or dioxane) or an amide (dimethylformamide), at a temperature of between 0° C. and the boiling point of the reaction mixture. The alkali metal alkoxide can be obtained by the action of a base (sodium or potassium hydroxide or methoxide) on the corresponding alcohol $R_6OH$.

The derivatives of formula (V) are commercially available or can be obtained by the methods described in "The Pyrazines" G. B. Barlin, Chapter 5, pp. 114–116 in "The Chemistry of Heterocyclic Compounds", edited by A. Weissberger and E. C. Taylor—1982 —Interscience Publishers, and in particular by halogenation of the corresponding dimethyl derivative using a halogenating agent such as N-chlorosuccinimide, in an inert solvent such as carbon tetrachloride, in the presence of an alkyl peroxide (for example benzoyl peroxide), at a temperature of between 40° C. and the boiling point of the reaction medium.

The derivatives $R_6OH$ (VI) are commercially available or can be obtained in particular by application or adaptation of the methods described in Houben-Weyl "Methoden der Organischen Chemie" Volume VI/1A, part 1, pp. 1–653—4th Edition—Georg Thieme Verlag—Stuttgart (1979), Volume VI/1A, part 2, pp. 771–1516—4th Edition—Georg Thieme Verlag—Stuttgart (1980) and volume VI/1B, pp. 1–976—4th Edition—Georg Thieme Verlag—Stuttgart (1984).

The compounds of formula (I) for which either R represents a CH residue, $R_1$ and $R_4$ are identical and each represent a radical —$CH_2$—O—$R_6$ and $R_2$ and $R_3$ each represent a hydrogen atom, or R represents a CH residue, $R_1$ and $R_3$ are identical and each represent a radical —$CH_2$—O—$R_6$ and $R_2$ and $R_4$ each represent a hydrogen atom, or R represents a CH residue, $R_2$ and $R_3$ are identical and each represent a radical —$CH_2$—O—$R_6$ and $R_1$ and $R_4$ each represent a hydrogen atom, can be prepared by the action of a derivative of formula (IV) in which either Re and Rh are identical and each represent a —$CH_2Cl$ radical and Rf and Rg each represent a hydrogen atom, or Re and Rg are identical and each represent a —$CH_2Cl$ radical and Rf and Rh each represent a hydrogen atom, or Rf and Rg are identical and each represent a —$CH_2Cl$ radical and Re and Rh each represent a hydrogen atom, on a derivative $R_6OH$ (VI) for which $R_6$ has the same meanings as in formula (I) and in which the hydroxyl functions are optionally protected in cyclic acetal form.

This reaction is carried out under the same conditions as those mentioned above for the reaction of (V) with (VI).

The derivatives of formula (IV) in which either Re and Rh are identical and each represent a —$CH_2Cl$ radical and Rf and Rg each represent a hydrogen atom, or Re and Rg are identical and each represent a —$CH_2Cl$ radical and Rf and Rh each represent a hydrogen atom, or Rf and Rg are identical and each represent a —CH$_2$Cl radical and Re and Rh each represent a hydrogen atom, can be obtained by application or adaptation of the methods described in "Pyridine and its Derivatives Supplement (Part Two)" in "The Chemistry of Heterocyclic Compounds" edited by A. Weissberger and E. C. Taylor—1974, pp. 456–475—Interscience Publishers, and in particular by halogenation of the corresponding dimethyl derivative using a halogenating agent such as N-chlorosuccinimide, in an inert solvent such as carbon tetrachloride and in the presence of an alkyl peroxide (for example benzoyl peroxide), at a temperature of between 40° C. and the boiling point of the reaction medium.

The compounds of formula (I) for which R represents a nitrogen atom, $R_1$ represents a radical —CH$_2$—NR$_5$R$_6$, —CH$_2$N(CH$_2$OH)$_2$, —CH$_2$—N(CH$_2$—(CHOH)$_y$—CH$_2$OH)$_2$, —CH$_2$—N(CH(CH$_2$OH)$_2$)$_2$ or —CH$_2$—N(CH$_2$—CH(CH$_2$OH)$_2$)$_2$ and one of the substituents $R_3$ or $R_4$ represents a hydrogen atom and the other is identical to $R_1$, and $R_2$ represents a hydrogen atom, can be prepared by the action of a derivative of formula (V) in which one of the substituents Ri and Rj represents a —CH$_2$Cl radical and the other represents a hydrogen atom, on an amine amine HNRcRd (III) in which Rc and Rd have the same meanings as above.

This reaction is generally carried out in an inert solvent such as an ether (for example tetrahydrofuran or dioxane) or a chlorinated solvent (for example carbon tetrachloride, methylene chloride, 1,2-dichloroethane or chloroform), at a temperature of between 0° C. and the boiling point of the reaction medium, optionally in the presence of an acid acceptor such as a nitrogenous organic base (for example trialkylamine, pyridine, 1,8-diazabicyclo[5.4.0]undec-7-ene or 1,5-diazabicyclo[4.3.0]non-5-ene).

The compounds of formula (I) for which either R represents a CH residue, $R_1$ and $R_4$ are identical and each represent a radical —CH$_2$—NR$_5$R$_6$, —CH$_2$—N(CH$_2$OH)$_2$, —CH$_2$—N(CH$_2$—(CHOH)$_y$—CH$_2$OH)$_2$, —CH$_2$—N(CH(CH$_2$OH)$_2$)$_2$, or —CH$_2$—N(CH$_2$—CH(CH$_2$OH)$_2$)$_2$ and $R_2$ and $R_3$ each represent a hydrogen atom, or R represents a CH residue, $R_1$ and $R_3$ are identical and each represent a radical —CH$_2$—NR$_5$R$_6$, —CH$_2$—N(CH$_2$OH)$_2$, —CH$_2$—N(CH$_2$—(CHOH)$_y$—CH$_2$OH)$_2$, —CH$_2$—N(CH(CH$_2$OH)$_2$)$_2$, or —CH$_2$—N(CH$_2$—CH(CH$_2$OH)$_2$)$_2$ and $R_2$ and $R_4$ each represent a hydrogen atom, or R represents a CH residue, $R_2$ and $R_3$ are identical and each represent a radical —CH$_2$—NR$_5$R$_6$, —CH$_2$—N(CH$_2$OH)$_2$, —CH$_2$—N(CH$_2$—(CHOH)$_y$—CH$_2$OH)$_2$, —CH$_2$—N(CH(CH$_2$OH)$_2$)$_2$ or —CH$_2$—N(CH$_2$—CH(CH$_2$OH)$_2$)$_2$ and $R_1$ and $R_4$ each represent a hydrogen atom, can be prepared by the action of a derivative of formula (IV) in which either Re and Rh are identical and each represent a —CH$_2$Cl radical and Rf and Rg each represent a hydrogen atom, or Re and Rg are identical and each represent a —CH$_2$Cl radical and Rf and Rh each represent a hydrogen atom, or Rf and Rg are identical and each represent a —CH$_2$Cl radical and Re and Rh each represent a hydrogen atom, on an amine amine HNRcRd (III) in which Rc and Rd have the same meanings as above.

This reaction is carried out under the same conditions as those mentioned above for the reaction of (V) with (III).

The compounds of formula (I) for which R represents a nitrogen atom, $R_1$ represents a radical —NR$_5$—CO—R$_6$ and one of the substituents $R_3$ or $R_4$ represents a hydrogen atom and the other is identical to $R_1$, and $R_2$ represents a hydrogen atom, can be prepared by the action of a derivative of formula:

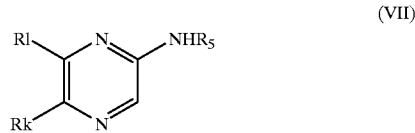

in which $R_5$ has the same meanings as in formula (I) and one of the substituents Rk or Rl represents a hydrogen atom and the other represents a radical NHR$_5$ in which $R_5$ has the same meanings as in formula (I), on an acid HOOC—R$_6$ (VIII) for which $R_6$ has the same meanings as in formula (I), or a reactive derivative of this acid and in particular a halide of this acid.

This reaction is generally carried out in the presence of a coupling agent used in peptide chemistry, such as a carbodiimide (for example N,N'-dicyclohexylcarbodiimide) or N,N'-carbonyldiimidazole, in an inert solvent such as an ether (for example tetrahydrofuran or dioxane), an amide (dimethylformamide) or a chlorinated solvent (for example methylene chloride, 1,2-dichloroethane or chloroform), at a temperature of between 0° C. and the reflux temperature of the reaction mixture, in the presence of an acid acceptor such as a nitrogenous organic base (for example a trialkylamine, pyridine, 1,8-diazabicyclo[5.4.0]undec-7-ene or 1,5-diazabicyclo[4.3.0]non-5-ene), in a solvent as mentioned above, or a mixture of these solvents, at a temperature of between 0° C. and the boiling point of the reaction mixture. When an acid chloride (VIII) is used, the process is generally performed in tetrahydrofuran, at a temperature of between 0° C. and the reflux temperature of the reaction mixture.

The derivatives of formula (VII) are commercially available or can be obtained in particular by application or adaptation of the methods described in "The Pyrazines" G. B. Barlin, Chapter 8, pp. 205–246 in "The Chemistry of Heterocyclic Compounds", edited by A. Weissberger and E. C. Taylor—1982—Interscience Publishers.

The derivatives HOOC—R$_6$ (VIII) are commercially available or can be obtained in particular by application or adaptation of the methods described in Houben-Weyl "Methoden der Organischen Chemie" Volume VIII Georg Thieme Verlag—Stuttgart (1952).

The compounds of formula (I) for which either R represents a CH residue, $R_1$ and $R_4$ are identical and each represent a radical —NR$_5$—CO—R$_6$ and $R_2$ and $R_3$ each represent a hydrogen atom, or R represents a CH residue, $R_1$ and $R_3$ are identical and each represent a radical —NR$_5$—CO—R$_6$ and $R_2$ and $R_4$ each represent a hydrogen atom, or R represents a CH residue, $R_2$ and $R_3$ are identical and each represent a radical —NR$_5$—CO—R$_6$ and $R_1$ and $R_4$ each represent a hydrogen atom, can be prepared by the action of a derivative of formula (IV) in which either Re and Rh are identical and each represent a radical —NHR$_5$ and Rf and Rg each represent a hydrogen atom, or Re and Rg are identical and each represent a radical —NHR$_5$ and Rf and Rh each represent a hydrogen atom, or Rf and Rg are identical and each represent a radical —NHR$_5$ and Re and Rh each represent a hydrogen atom, on a derivative HOOC—R$_6$ (VIII) for which $R_6$ has the same meanings as in formula (I), or a reactive derivative of this acid such as a chloride.

This reaction is carried out under the same conditions as those mentioned above for the reaction of (VII) with (VIII).

The derivatives of formula (IV) in which either Re and Rh are identical and each represent a radical —NHR$_5$ and Rf and Rg each represent a hydrogen atom, or Re and Rg are identical and each represent a radical —NHR$_5$ and Rf and Rh each represent a hydrogen atom, or Rf and Rg are identical and each represent a radical —NHR$_5$ and Re and Rh each represent a hydrogen atom, can be obtained by application or adaptation of the methods described in "Pyridine and its Derivatives Supplement (Part Three)" in "The Chemistry of Heterocyclic Compounds" edited by A. Weissberger and E. C. Taylor—1974, pp. 41–256—Interscience Publishers.

The compounds of formula (I) for which R represents a nitrogen atom, R$_1$ represents a radical —CH$_2$—O—R$_6$ in which R$_6$ represents a radical -alk-O-alk and one of the substituents R$_3$ or R$_4$ represents a hydrogen atom and the other is identical to R$_1$, and R$_2$ represents a hydrogen atom, can be prepared by the action of a derivative of formula:

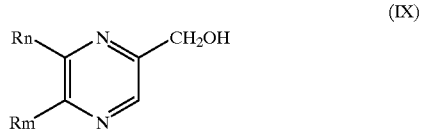

(IX)

in which one of the substituents Rm or Rn represents a —CH$_2$OH radical and the other represents a hydrogen atom, on a derivative Hal-alk-O-alk (X) for which alk represents an alkyl radical and Hal represents a halogen atom and preferably a chlorine or bromine atom.

This reaction is generally carried out in an inert solvent such as tetrahydrofuran, at 20° C.

The derivatives of formula (IX) are commercially available or can be obtained by the methods described in "The Pyrazines" G. B. Barlin in "The Chemistry of Heterocyclic Compounds" edited by A. Weissberger and E. C. Taylor—1982—Interscience Publishers.

The derivatives Hal-alk-O-alk are commercially available or can be obtained according to the methods described in Houben-Weyl "Methoden der Organischen Chemie" Volume V/4 Georg Thieme Verlag—Stuttgart (1960).

The compounds of formula (I) for which either R represents a CH residue, R$_1$ and R$_4$ are identical and each represent a radical —CH$_2$—O—R$_6$ in which R$_6$ represents a radical -alk-O-alk and R$_2$ and R$_3$ each represent a hydrogen atom, or R represents a CH residue, R$_1$ and R$_3$ are identical and each represent a radical —CH$_2$—O—R$_6$ in which R$_6$ represents a radical -alk-O-alk and R$_2$ and R$_4$ each represent a hydrogen atom, or R represents a CH residue, R$_2$ and R$_3$ are identical and each represent a radical —CH$_2$—O—R$_6$ in which R$_6$ represents a radical -alk-O-alk and R$_1$ and R$_4$ each represent a hydrogen atom, can be prepared by the action of a derivative of formula (IV) in which either Re and Rh are identical and each represent a —CH$_2$OH radical and Rf and Rg each represent a hydrogen atom, or Re and Rg are identical and each represent a —CH$_2$OH radical and Rf and Rh each represent a hydrogen atom, or Rf and Rg are identical and each represent a —CH$_2$OH radical and Re and Rh each represent a hydrogen atom, on a derivative Hal-alk-O-alk (X) for which alk represents an alkyl radical and Hal represents a halogen atom and preferably a bromine or chlorine atom.

This reaction is carried out under the same conditions as those mentioned above for the reaction of (IX) with (X).

The derivatives of formula (IV) in which either Re and Rh are identical and each represent a —CH$_2$OH radical and Rf and Rg each represent a hydrogen atom, or Re and Rg are identical and each represent a —CH$_2$OH radical and Rf and Rh each represent a hydrogen atom, or Rf and Rg are identical and each represent a —CH$_2$OH radical and Re and Rh each represent a hydrogen atom, can be obtained according to the methods described by Tsuda et al. Pharm. Bull. 1, 142 (1953); Momenteau et al. J. Chem. Soc. Perkin Trans 1, 61 (1985); Dawson et al. J. Med. Chem. 26, 1282 (1983); Mathes et al. Chem. Ber. 86, 584 (1953); Baker et al. J. Chem. Soc. 3594 (1958); Boekelheide et al. J. Am. Chem. Soc. 76, 1286 (1954).

The various stereoisomers of the compounds of formula (I) are obtained from the corresponding stereoisomers of the various intermediates.

A person skilled in the art understands that, in order to carry out the processes according to the invention which are described above, it may be necessary to introduce protecting groups for the hydroxyl functions in order to avoid side reactions. These groups are those which can be removed without affecting the rest of the molecule. As examples of, protecting groups for the hydroxyl function, mention may be made of trialkylsilyl (for example triethylsilyl) and benzyl. Other protecting groups which can be used in these processes are also described by W. Greene et al., Protective Groups in Organic Synthesis, second edition, 1991, John Wiley & Sons and P. J. Kocienski, Protecting groups, edited by Thieme Verlag (1994).

The reaction mixtures obtained by the various processes described above are treated according to standard physical methods (for example evaporation, extraction, distillation, chromatography or crystallization) or chemical methods (for example formation of salts).

The compounds of formula (I) can optionally be converted into addition salts with an inorganic or organic acid by the action of such an acid in an organic solvent such as an alcohol, a ketone, an ether or a chlorinated solvent. These salts also form part of the invention.

As examples of pharmaceutically acceptable salts, mention may be made of the addition salts with inorganic or organic acids such as acetate, propionate, succinate, benzoate, fumarate, maleate, oxalate, methanesulphonate, isethionate, theophyllinacetate, salicylate, methylenebis-β-oxynaphthoate, hydrochloride, sulphate, nitrate and phosphate.

The examples which follow illustrate the invention:

EXAMPLE 1

A solution of 392 mg of 2,5-dimethoxycarbonylpyrazine and 485 mg of tris(hydroxymethyl)aminomethane in 3 cm$^3$ of ethanol is heated at a temperature close to the reflux temperature for 90 minutes. The reaction mixture is cooled to a temperature of 20° C. and 10 cm$^3$ of ethanol are then added over 2 minutes. The reaction mixture is stirred at 20° C. for 1 hour. The white solid formed is filtered off, washed successively with twice 10 cm$^3$ of boiling ethanol and twice 10 cm$^3$ of diethyl ether. 650 mg of N,N'-bis[(tris(hydroxymethyl)methyl]-pyrazine-2,5-dicarboxamide are thus obtained in the form of a white solid melting at a temperature above 260° C. [$^1$H NMR spectrum (250 MHz, (CD$_3$)$_2$SO-d$_6$, δ in ppm): 3.76 (d, J=5.5 Hz, 12H: 6×OCH$_2$); 4.90 (t, J=5.5 Hz, 6H: 6×OH); 8.25 (s, 2H: =CH at 3 and =CH at 6); 9.26 (s, 2H: 2×CONH)].

2,5-Dimethoxycarbonylpyrazine can be obtained according to W. J. Schut, H. I. X. Mager and W. Berends, Rec. Trav. Chim. Netherlands, 80, 391 (1961).

EXAMPLE 2

A solution of 392 mg of 2,5-dimethoxycarbonylpyrazine and 780 mg of N-methylglucamine in 5 cm$^3$ of ethanol is heated at a temperature close to the reflux temperature for 3 hours and the reaction mixture is filtered while hot. The white solid is washed with twice 10 cm$^3$ of boiling ethanol. 1000 mg of N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]-pyrazine-2,5-dicarboxamide are thus obtained in the form of a white solid melting at 152° C. [$^1$H NMR spectrum (400 MHz, (CD$_3$)$_2$SO-d$_6$, at a temperature of 403 K, δ in ppm): 3.14 (s, 6H: 2×NCH$_3$); from 3.45 to 4.28 (mts, 16H: 8×CHO–2×CH$_2$ and 2×CH$_2$N); 8.78 (s, 2H: =CH at 3 and =CH at 6)].

EXAMPLE 3

A solution of 392 mg of 2,5-dimethoxycarbonylpyrazine and 364 mg of 2-amino-1,3-propanediol in 5 cm$^3$ of ethanol is heated at a temperature in the region of the reflux temperature for 3 hours. The reaction mixture is filtered while hot. The white solid is washed with 3 times 10 cm$^3$ of boiling ethanol. 530 mg of N,N'-bis(1,3-dihydroxy-2-propyl)pyrazine-2,5-dicarboxamide are thus obtained in the form of a white solid melting at 218° C. [$^1$H NMR spectrum (400 MHz, (CD$_3$)$_2$SO-d$_6$, δ in ppm): from 3.45 to 3.65 (mt, 8H: 4×CH$_2$O); 4.02 (mt, 2H: 2×NCH); 4.85 (t, J=5.5 Hz, 4H: 4×OH); 8.48 (d, J=9 Hz, 2H: 2×CONH); 9.25 (s, 2H: =CH at 3 and =CH at 6)].

EXAMPLE 4

A solution of 490 mg of 2,5-dimethoxycarbonylpyrazine and 0.40 cm$^3$ of 3-amino-1,2-propanediol in 5 cm$^3$ of ethanol is heated at a temperature in the region of the reflux temperature for 3 hours. The reaction mixture is filtered while hot. The white solid is washed with 3 times 15 cm$^3$ of boiling ethanol. 416 mg of N,N'-bis(2,3-dihydroxy-1-propyl)pyrazine-2,5-dicarboxamide are thus obtained in the form of a white solid melting at 234° C. [$^1$H NMR spectrum (400 MHz, (CD$_3$)$_2$SO-d$_6$, δ in ppm): from 3.20 to 3.60 (mt, 8H: 2×OCH$_2$ and 2×NCH$_2$); 3.68 (mt, 2H: 2×OCH); 4.67 (t, J=5.5 Hz, 2H: OH at 2γ and OH at 5γ); 4.95 (d, J=5 Hz, 2H: OH at 2β and OH at 5β); 8.79 (t, J=5.5 Hz, 2H: 2×CONH); 9.23 (s, 2H: =CH at 3 and =CH at 6)].

EXAMPLE 5

A solution of 500 mg of 2,5-dimethoxycarbonylpyrazine and 0.48 cm$^3$ of diethanolamine in 3 cm$^3$ of ethanol is heated to a temperature in the region of the reflux temperature for 3 hours. The reaction mixture is cooled to 20° C. and the white solid formed is then filtered off and washed with 2 cm$^3$ of ethanol. 600 mg of N,N,N',N'-tetrakis(2-hydroxyethyl)pyrazine-2,5-dicarboxamide are thus obtained in the form of a white solid melting at 143° C. [$^1$H NMR spectrum (250 MHz, (CD$_3$)$_2$SO-d$_6$, at a temperature of 403 K, δ in ppm): from 3.50 to 3.80 (mt, 16H: 4×NCH$_2$CH$_2$O); 4.32 (mt, 4H: 4×OH); 8.76 (s, 2H: =CH at 3 and =CH at 6)].

EXAMPLE 6

A solution of 500 mg of 2,5-dimethoxycarbonylpyrazine and 525 mg of 2-amino-2-methyl-1,3-propanediol in 3 cm$^3$ of ethanol is heated at a temperature in the region of the reflux temperature for 90 minutes. The reaction mixture is filtered while hot. The white solid is washed with 5 cm$^3$ of boiling ethanol. 200 mg of N,N'-bis(1,3-dihydroxy-2-methyl-2-propyl)pyrazine-2,5-dicarboxamide are thus obtained in the form of a white solid melting at 208° C. [$^1$H NMR spectrum (400 MHz, CDCl$_3$, δ at ppm): 1.34 (s, 6H: 2×CH$_3$); 3.55 and 3.66 (2 dd, J=11 and 5.5 Hz, 8H: 4×OCH$_2$); 5.01 (t, J=5.5 Hz, 4H: 4×OH); 8.22 (s, 2H: =CH at 3 and =CH at 6); 9.20 (s, 2H: 2×CONH)].

EXAMPLE 7

A solution of 500 mg of 2,5-dimethoxycarbonylpyrazine and 525 mg of 3-methylamino-1,2-propanediol in 3 cm$^3$ of ethanol is heated at a temperature in the region of the reflux temperature for 2 hours. The reaction mixture is cooled to 20° C. and the solution obtained is then concentrated under reduced pressure (2.7 kPa) at 40° C. The residue is taken up in 5 cm$^3$ of ethanol. The suspension is refluxed and filtered while hot. After cooling the filtrate, the white solid formed is filtered and then washed with twice 10 cm$^3$ of ethanol. 230 mg of bis{N-[2(R,S)-3-dihydroxy-1-propyl]-N-methyl}pyrazine-2,5-dicarboxamide are thus obtained in the form of a white solid melting at 158° C. [$^1$H NMR spectrum (400 MHz, (CD$_3$)$_2$SO-d$_6$, at a temperature of 393 K, δ in ppm): 3.12 (s, 6H: 2×CONCH$_3$); from 3.30 to 3.65 (unres. mult., 8H: NCH$_2$ at 2α-NCH$_2$ at 5α-OCH$_2$ at 2γ and OCH$_2$ at 5γ); 3.82 (unres. mult., 2H: CH 2β and CH 5β); 3.98 and 4.29 (2 unres. mults., 2H each: 4×OH); 8.77 (s, 2H: =CH at 3 and =CH at 6)].

EXAMPLE 8

A solution of 500 mg of 2,5-dimethoxycarbonylpyrazine and 0.430 cm$^3$ of 2-methoxyethylamine in 3 cm$^3$ of ethanol is heated at a temperature in the region of the reflux temperature for 5 hours. The reaction mixture is cooled to a temperature of 20° C. and the white solid formed is then filtered off and washed with twice 5 cm$^3$ of ethanol. 150 mg of N,N'-bis-(2-methoxyethyl)pyrazine-2,5-dicarboxamide are thus obtained in the form of a white solid melting at 165° C. [$^1$H NMR spectrum (300 MHz, (CD$_3$)$_2$SO-d$_6$, δ in ppm): 3.29 (s, 6H: 2×OCH$_3$); 3.51 (mt, 8H: 2×NCH$_2$CH$_2$O); 8.99 (mt, 2H: 2×CONH); 9.22 (s, 2H: =CH at 3 and =CH at 6)].

EXAMPLE 9

A solution of 500 mg of 2,5-dimethoxycarbonylpyrazine and 0.720 cm$^3$ of 2-(2-aminoethoxy)ethanol in 3 cm$^3$ of ethanol is heated at a temperature in the region of the reflux temperature for 4 hours. The reaction mixture is cooled to a temperature of 20° C. and the white solid formed is then filtered off and washed with twice 5 cm$^3$ of ethanol. 150 mg of N,N'-bis(2-hydroxyethyloxyethyl)-pyrazine-2,5-dicarboxamide are thus obtained in the form of a white solid melting at 125° C. [$^1$H NMR spectrum (300 MHz, (CD$_3$)$_2$SO-d$_6$, δ at ppm): from 3.35 to 3.65 (mt, 16H: 2×NCH$_2$CH$_2$OCH$_2$CH$_2$O); 4.62 (t, J=5.5 Hz, 2H: 2×OH); 9.00 (t, J=6 Hz, 2H: 2×NHCO); 9.20 (s, 2H: =CH at 3 and =CH at 6)].

EXAMPLE 10

A solution of 500 mg of 2,6-dimethoxycarbonylpyrazine and 525 mg of 2-amino-2-methyl-1,3-propanediol in 5 cm$^3$ of ethanol is heated at a temperature in the region of the reflux temperature for 3 hours. The reaction mixture is cooled to a temperature of 20° C. and the white solid formed is then filtered off and washed with twice 5 cm$^3$ of ethanol. 260 mg of N,N'-bis(1,3-dihydroxy-2-methyl-2-propyl)pyrazine-2,6-dicarboxamide are thus obtained in the form of a white solid melting at 169° C. [$^1$H NMR spectrum (400 MHz, (CD$_3$)$_2$SO-d$_6$, δ in ppm): 1.34 (s, 6H: 2×CH$_3$); 3.61 and 3.69 (2 dd, J=11 and 5.5 Hz, 8H: 4×CH$_2$O); 4.88 (t, J=5.5 Hz, 4H: 4×OH); 8.16 (s, 2H: 2×CONH); 9.35 (s, 2H: =CH at 3 and =CH at 5)].

2,6-Dimethoxycarbonylpyrazine can be obtained as described by H. I. X. Mager and W. Berends, Rec. Trav. Chim. Netherlands, 77,827 (1958).

EXAMPLE 11

3.61 g of pyridine-2,5-dicarboxylic acid dichloride are added to a solution of 3.50 g of 2-amino-2-methyl-1,3-propanediol in 100 cm³ of toluene, followed by dropwise addition of 7 cm³ of triethylamine over 10 minutes. The reaction mixture is heated for 5 hours at a temperature in the region of the reflux temperature. The reaction mixture is cooled to a temperature of 20° C. and is then concentrated under reduced pressure (2.7 kPa) at a temperature of 40° C. The oily residue (12 g) is chromatographed on a column of silica (0.02–0.045 mm) 4 cm in diameter, eluted with a chloroform/methanol/ 20% aqueous ammonia mixture (12:6:1 by volume). The fractions containing the product (fractions 1 to 20) are concentrated under reduced pressure (2.7 kPa) at 40° C. The residue (4.6 g) is chromatographed on a column of silica (0.02–0.045 mm) 4 cm in diameter, eluted with a chloroform/methanol mixture (9:1 by volume), collecting 100 cm³ fractions. The fractions containing the product are concentrated under reduced pressure (2.7 kPa) at 40° C. 1.4 g of N,N'-bis(1,3-dihydroxy-2-methyl-2-propyl)pyridine-2,5-carboxamide are thus obtained in the form of a pale yellow oil (Rf=0.15; thin layer chromatography on silica; eluent: 9:1 (by volume) dichloromethane/methanol) [$^1$H NMR spectrum (400 MHz, CDCl$_3$, δ at ppm): 1.30 and 1.34 (2s, 3H each: 2×CH$_3$); from 3.45 to 3.70 (mt, 8H: 4×CH$_2$O); 4.75 and 5.00 (2t, J=5.5 Hz, 2H each: 4×OH); 7.73 (s, 1H: CONH); 8.10 (d, J=8 Hz, 1H: =CH at 3); 8.35 (dd, J=8 and 2 Hz, 1H: =CH at 4); 8.38 (s, 1H: CONH); 8.95 (d, J=2 Hz, 1H: =CH at 6)].

EXAMPLE 12

3.61 g of pyridine-2,5-dicarboxylic acid dichloride are added to a solution of 3.07 g of 2-amino-1,3-propanediol in 100 cm³ of toluene, followed by dropwise addition of 7 cm³ of triethylamine over 10 minutes. The reaction mixture is heated for 5 hours at a temperature in the region of the reflux temperature. The reaction mixture is cooled to 20° C. and is then concentrated under reduced pressure (2.7 kPa) at 40° C. The oily residue (11.6 g) is chromatographed on a column of silica (0.02–0.045 mm) 4 cm in diameter, eluted with a chloroform/methanol/20% aqueous ammonia mixture (24:6:1 by volume) for the first 50 fractions and a chloroform/methanol/20% aqueous ammonia mixture (12:6:1 by volume) for the following fractions. The fractions containing the product (fractions 50 to 70) are concentrated under reduced pressure (2.7 kPa) at 40° C. 5.3 g of N,N'-bis(1,3-dihydroxy-2-propyl)pyridine-2,5-dicarboxamide are thus obtained in the form of a cream- yellow solid (Rf=0.56; thin layer chromatography on silica; eluent: chloroform/methanol/20% aqueous ammonia (12:6:1 by volume)) [$^1$H NMR spectrum (400 MHz, (CD$_3$)$_2$SO-d$_6$, δ in ppm): 3.55 (mt, 8H: 4×CH$_2$O); 4.00 (mt, 2H: 2×NCH); from 4.45 to 5.05 (unres. mult., 4H: 4×OH); 8.13 (d, J=8 Hz, 1H: =CH at 3); from 8.35 to 8.50 (mt, 3H: 2×CONH and =CH at 4); 9.05 (broad s, 1H: =CH at 6)].

Pyridine-2,5-dicarboxylic acid dichloride can be obtained according to H. Meyer and F. Staffen, Mont. Chem., 34, 517 (1913).

EXAMPLE 13

2 g of pyridine-2,6-dicarboxylic acid dichloride are added, over 5 minutes, to a solution of 2 g of 2-amino-1,3-propanediol in 100 cm³ of toluene, followed by dropwise addition of 4.6 cm³ of triethylamine over 10 minutes. The reaction mixture is heated for 5 hours at a temperature in the region of the reflux temperature. The reaction mixture is cooled to 20° C. and is then concentrated under reduced pressure (2.7 kPa) at 40° C. The residue is dissolved in 100 cm³ of ethanol and the insoluble material is filtered off. The solid (1.2 g) is dissolved in 250 cm³ of distilled water and the solution is freeze-dried (−36° C. to +25° C. over 16 h at 2.7 kPa). 750 mg of N,N'-bis(1,3-dihydroxy-2-propyl)pyridine-2,6-dicarboxamide are thus obtained in the form of a cream-coloured solid (Rf=0.76; thin layer chromatography on silica; eluent: chloroform/methanol/20% aqueous ammonia (12:6:1 by volume)); [$^1$H NMR spectrum (400 MHz, (CD$_3$)$_2$SO-d$_6$, δ in ppm) 3.63 (mt, 8H: 4×CH$_2$O); 4.00 (mt, 2H: 2×NCH); 4.83 (mt, 4H: 4×OH); from 8.10 to 8.30 (mt, 3H: aromatic H of the pyridine); 8.63 (d, J=8 Hz, 2H: 2×CONH)].

Pyridine-2,6-dicarboxylic acid dichloride can be obtained according to H. Meyer, Mont. Chem., 24, 195 (1903).

EXAMPLE 14

2 g of pyridine-2,6-dicarboxylic acid dichloride are added, over 5 minutes, to a solution of 2.3 g of 2-amino-2-methyl-1,3-propanediol in 100 cm³ of toluene, followed by dropwise addition of 4.6 cm³ of triethylamine over 10 minutes. The reaction mixture is heated for 5 hours at a temperature in the region of the reflux temperature. The reaction mixture is cooled to 20° C. The oily solid formed is separated out after settling of the phases has taken place and taken up in 100 cm³ of methanol, and the solution is concentrated under reduced pressure (2.7 kPa) at 40° C. The residue is triturated with 20 cm³ of ethanol. The solid is filtered off and then chromatographed on a column of silica (0.02–0.045 mm) 3 cm in diameter, eluted with a chloroform/methanol mixture (9:1 by volume). The fractions containing the product are concentrated under reduced pressure (2.7 kPa) at 40° C. The residue is triturated with 10 cm³ of a dichloromethane/methanol mixture (19:1 by volume). The solid is filtered off is dried to constant weight at 40° C. 90 mg of N,N'-bis(1,3-dihydroxy-2-methyl-2-propyl)pyridine-2,6-dicarboxamide are thus obtained in the form of a white solid melting at 184° C. [$^1$H NMR spectrum (400 MHz, (CD$_3$)$_2$SO-d$_6$, δ in ppm): 1.34 (s, 6H: 2×CH$_3$); 3.60 (dd, J=11 and 6 Hz, 4H: 4H of 4×CH$_2$O); 3.68 (dd, J=10 and 6 Hz, 4H: the other 4×H of the 4×CH$_2$O); 4.92 (t, J=6 Hz, 4H: 4 OH); 8.20 (s, 3H: aromatic H of the pyridine); 8.24 (s, 2H: 2×CONH)].

EXAMPLE 15

2 g of pyridine-3,5-dicarboxylic acid dichloride are added, over 5 minutes, to a solution of 2 g of 2-amino-1,3-propanediol in 100 cm³ of toluene, followed by dropwise addition of 4.6 cm³ of triethylamine over 10 minutes. The reaction mixture is heated for 5 hours at a temperature in the region of the reflux temperature. The reaction mixture is cooled to 20° C. and is then concentrated under reduced pressure (2.7 kPa) at 40° C. The residue is chromatographed on a column of silica (0.02–0.045 mm) 3 cm in diameter, eluted with a chloroform/methanol/20% aqueous ammonia mixture (12:6:1 by volume) and then with methanol. The fractions containing the product are concentrated under reduced pressure (2.7 kPa) at 40° C. The residue (1.48 g) is triturated with 10 cm³ of ethanol. The solid formed is filtered off, washed with 5 cm³ of ethanol and dried under reduced pressure (2.7 kPa) at 40° C. 240 mg of N,N'-bis(1,3-dihydroxy-2-propyl)pyridine-3,5-dicarboxamide are thus obtained in the form of a cream-coloured solid melting at 196° C. [$^1$H NMR spectrum (400 MHz, (CD$_3$)$_2$SO-d$_6$, δ in ppm): 3.55 (mt, 8H: 4×CH$_2$O); 4.01 (mt, 2H: 2×NCH); 4.70

(t, J=5.5 Hz, 4H: 4×OH); 8.36 (d, J=Hz, 2H: 2×CONH); 8.63 (t, J=2 Hz, 1H: =CH at 4); 9.11 (d, J=2 Hz, 2H: =CH at 2 and =CH at 6)].

Pyridine-3,5-dicarboxylic acid dichloride can be obtained according to H. Meyer and H. Tropsch, Mont. Chem., 35, 781 (1914).

EXAMPLE 16

2 g of pyridine-3,5-dicarboxylic acid dichloride are added, over 5 minutes, to a solution of 2.3 g of 2-amino-2-methyl-1,3-propanediol in 100 cm$^3$ of toluene, followed by dropwise addition of 6.2 cm$^3$ of triethylamine over 10 minutes. The reaction mixture is heated for 5 hours at a temperature in the region of the reflux temperature. The reaction mixture is cooled to 20° C. and is then concentrated under reduced pressure (2.7 kPa) at 40° C. The residue is chromatographed on a column of silica (0.02–0.045 mm) 3 cm in diameter, eluted with a chloroform/methanol/20% aqueous ammonia mixture (12:6:1 by volume). The fractions containing the product are concentrated under reduced pressure (2.7 kPa) at 40° C. N,N'-Bis[1,3-dihydroxy-2-methyl-2-propyl]pyridine-3,5-dicarboxamide is thus obtained.

EXAMPLE 17

110 mg of benzoyl peroxide and 4.43 g of N-chlorosuccinimide are added to a solution of 1.80 g of 2,5-dimethylpyrazine in 50 cm$^3$ of carbon tetrachloride. The reaction mixture is heated for 24 hours at a temperature in the region of the reflux temperature. The reaction mixture is cooled to 20° C. and is then filtered. A solution of 3.42 g of 2-amino-1,3-propanol in 60 cm$^3$ of carbon tetrachloride is added to the solution obtained. The reaction mixture is heated at a temperature in the region of the reflux temperature for 4 hours and is then concentrated under reduced pressure (2.7 kPa) at 40° C. The oily residue (7.0 g) is chromatographed on a column of silica (0.02–0.045 mm) 3.5 cm in diameter, eluted with a chloroform/methanol/20% aqueous ammonia mixture (24:6:1 by volume), collecting 100 cm$^3$ fractions. The fractions containing the product are concentrated under reduced pressure (2.7 kPa) at 40° C. The orange oil obtained (1.0 g) is taken up in 15 cm$^3$ of boiling ethanol. The mixture is treated with 500 mg of animal charcoal and filtered while hot. The filtrate is left to stand for 2 hours at 20° C. The solid formed is filtered off, rinsed with twice 2 cm$^3$ of ethanol and then dried under reduced pressure (2.7 kPa) at 40° C. 260 mg of N,N'-bis(1,3-dihydroxy-2-propyl)pyrazine-2,5-dimethanamine are thus obtained in the form of a white solid melting at 132° C. [$^1$H NMR spectrum (300 MHz, (CD$_3$)$_2$SO-d$_6$, δ in ppm); 2.56 (mt, 2H: 2×NCH); from 3.20 to 3.50 (mt, 8H: 4×OCH$_2$); 3.90 (s, 4H: 2×ArCH$_2$N); 4.48 (t, J=5 Hz, 4H: 4×OH); 8.62 (s, 2H: =CH at 3 and =CH at 6)].

EXAMPLE 18

220 mg of benzoyl peroxide and 8.86 g of N-chlorosuccinimide are added to a solution of 3.60 g of 2,5-dimethylpyrazine in 100 cm$^3$ of carbon tetrachloride. The reaction mixture is heated for 24 hours at a temperature in the region of the reflux temperature. The reaction mixture is cooled to 20° C. and then filtered. A solution of 24.11 cm$^3$ of diethanolamine in 130 cm$^3$ of carbon tetrachloride is added to the solution obtained. The reaction mixture is heated at a temperature in the region of the reflux temperature for 4 hours and is then concentrated under reduced pressure (2.7 kPa) at 40° C. The oily residue is chromatographed on a column of silica (0.02–0.045 mm) 3.5 cm in diameter, eluted with a chloroform/methanol/20% aqueous ammonia mixture (24:6:1 by volume), collecting 200 cm$^3$ fractions. The fractions containing the product are concentrated under reduced pressure (2.7 kPa) at 40° C. The brown oil obtained (1.0 g) is taken up in 30 cm$^3$ of ethanol and 5 cm$^3$ of a 2N hydrochloric ether solution and then 5 cm$^3$ of diethyl ether. The mixture is left for 1 hour at 5° C. The solid formed is filtered off and rinsed with twice 10 cm$^3$ of diethyl ether. The solid is recrystallized from 30 cm$^3$ of ethanol. 400 mg of N,N,N',N'-tetrakis(2-hydroxyethyl)pyrazine-2,5-dimethanamine are thus obtained in the form of a white solid melting at 185° C. [$^1$H NMR spectrum (400 MHz, (CD$_3$)$_2$SO-d$_6$ with addition of a few drops of CD$_3$COOD-d$_4$, δ in ppm): 3.39 and 3.85 (broad t and t respectively, J=5 Hz, 8H each: 4×NCH$_2$CH$_2$O); 4.74 (s, 4H: 2×ArCH$_2$N); 8.97 (s, 2H: =CH at 3 and =CH at 6). For the spectrum in (CD$_3$)$_2$SO-d$_6$, we also observe: from 5.20 to 5.60 (broad unres. mult., 4H: 4×OH); from 10.30 to 10.50 (unres. mult., 2H: 2×NH$^+$Cl$^-$)].

EXAMPLE 19

50 mg of benzoyl peroxide and 6.81 g of N-chlorosuccinimide are added to a solution of 2.76 g of 2,6-dimethylpyrazine in 60 cm$^3$ of carbon tetrachloride. The reaction mixture is heated for 24 hours at a temperature in the region of the reflux temperature. The reaction mixture is cooled to 20° C. and then filtered. 100 cm$^3$ of carbon tetrachloride are added to the solution obtained, followed by a solution of 9.30 g of 2-amino-1,3-propanol in 50 cm$^3$ of carbon tetrachloride. The reaction mixture is heated at a temperature in the region of the reflux temperature for 6 h and is then concentrated under reduced pressure (2.7 kPa) at 40° C. The oily residue (13 g) is chromatographed on a column of silica (0.02–0.045 mm) 5 cm in diameter, eluted with a chloroform/methanol/20% aqueous ammonia mixture (24:6:1 by volume) for the first 60 fractions and a chloroform/methanol/20% aqueous ammonia mixture (12:6:1 by volume) for the following fractions, collecting 100 cm$^3$ fractions. The fractions containing the product (fractions 61 to 75) are concentrated under reduced pressure (2.7 kPa) at 40° C. The orange oil obtained (4.7 g) is chromatographed on a column of silica (0.02–0.045 mm) 4 cm in diameter, eluted with a chloroform/methanol/20% aqueous ammonia mixture (12:6:1 by volume), collecting 100 cm$^3$ fractions. The fractions containing the product are concentrated under reduced pressure (2.7 kPa) at 40° C. The residue is triturated successively with 10 cm$^3$ of acetone and diethyl ether. The residual solid is dissolved in 10 cm$^3$ of ethanol. 30 cm$^3$ of isopropyl ether are added dropwise to the solution obtained and the mixture is then left for 48 hours at 20° C. The orange solid formed is filtered off, rinsed with 3 times 5 cm$^3$ of a methanol/isopropyl ether mixture (1:9 by volume) and then dried under reduced pressure (2.7 kPa) at 40° C. 260 mg of N,N'-bis(1,3-dihydroxy-2-propyl)pyrazine-2,5-dimethanamine are thus obtained in the form of an orange solid melting at 87° C. [$^1$H NMR spectrum (400 MHz, (CD$_3$)$_2$SO-d$_6$, δ in ppm): 2.58 (mt, 2H: 2×NCH); from 3.30 to 3.50 (mt, 8H: 4×CH$_2$O); 3.92 (s, 4H: 2×ArCH$_2$N); 4.48 (unres. mult., 4H: 4×OH); 8.58 (s, 2H: =CH at 3 and =CH at 5)].

EXAMPLE 20

A solution of 1.78 g of 2,6-dichloromethylpyridine, 2.34 g of 2-amino-2-methyl-1,3-propanediol and 2.8 cm$^3$ of triethylamine in 50 cm$^3$ of ethanol is heated for 48 hours at a temperature in the region of the reflux temperature. The reaction mixture is cooled to 20° C. and then concentrated under reduced pressure (2.7 kPa) at 40° C. The oily residue (6 g) is chromatographed on a column of silica (0.02–0.045 mm) 4 cm in diameter, eluted with a chloroform/methanol/ 20% aqueous ammonia mixture (12:6:1 by volume). The fractions containing the product are concentrated under reduced pressure (2.7 kPa) at 40° C. The colourless oil obtained (0.7 g) is triturated successively with 10 cm$^3$ of acetone and diethyl ether. The residual solid is dissolved in 50 cm$^3$ of ethanol. 30 cm$^3$ of isopropyl ether are added dropwise to the solution obtained and the mixture is then left for 48 hours at 20° C. The white solid formed is filtered off, rinsed with 5 times 5 cm$^3$ of diethyl ether and then dried under reduced pressure (2.7 kPa) at 40° C. 440 mg of N,N'-(1,3-dihydroxy-2-methyl-2-propyl)pyridine-2,6-dimethanamine are thus obtained in the form of a white solid melting at 97° C. [$^1$H NMR spectrum (400 MHz, (CD$_3$)$_2$SO-d$_6$, δ in ppm): 0.94 (s, 6H: 2×CH$_3$); from 3.20 to 3.40 (s, 8H: 4×CH$_2$O); 3.76 (s, 4H: 2×ArCH$_2$N); 4.49 (unres. mult., 4H: 4×OH); 7.28 (d, J=8 Hz, 2H: =CH at 3 and =CH at 5); 7.67 (t, J=8 Hz, 1H: =CH at 4)].

EXAMPLE 21

A solution of 550 mg of 2,6-bis(2', 2'-dimethyl-1', 3'-dioxolan-4'-ylmethyloxymethyl)pyridine in 9 cm$^3$ of 1N hydrochloric acid is stirred for 3 hours at 20° C. and is then concentrated under reduced pressure (2.7 kPa) at 40° C. The oily residue is taken up successively in 3×30 cm$^3$ of ethanol and 50 cm$^3$ of diethyl ether and concentrated under reduced pressure (2.7 kPa) at 40° C. 480 mg of 2,6-bis(2,3-dihydroxy-1-propyloxymethyl)-pyridinium hydrochloride are thus obtained in the form of a colourless oil. [$^1$H NMR spectrum (400 MHz, (CD$_3$)$_2$SO-d$_6$, δ in ppm): 3.39 (d, J=6 Hz, 4H: OCH$_2$2γ and OCH$_2$6γ); from 3.45 to 3.75 (2 mts, 2H and 4H respectively: CH 2γ-CH 6γ-CH$_2$O 2ϵ and CH$_2$O 6ϵ); 4.83 (s, 4H: 2×ArCH$_2$O); 7.80 (d, J=8 Hz. 2H: =CH at 3 and =CH at 5); 8.35 (t, J=8 Hz, 1H: =CH at 4)].

2,6-Bis(2', 2'-dimethyl-1', 3'-dioxolan-4'-ylmethyloxymethyl)pyridine can be prepared in the following way: 4.95 g of potassium hydroxide are added. to a solution of 3.30 g of (S)-(+)-2,2-dimethyl-1,3-dioxolane-4-methanol in 125 cm$^3$ of o-xylene and the reaction mixture is then heated for 4 hours at 130° C. The reaction mixture is cooled to 20° C. and 2.20 g of 2,6-bis(chloromethyl)pyridine are then added. The reaction medium is heated for 3 hours at 130° C. and is then concentrated under reduced pressure (2.7 kPa) at 60° C. The oily residue (6 g) is taken up in 150 cm$^3$ of distilled water. This solution is extracted with 180 cm$^3$ in total of diethyl ether. The combined organic phases are washed with 180 cm$^3$ in total of distilled water, dried over magnesium sulphate and then concentrated under reduced pressure (2.7 kPa) at 60° C. The oily residue is chromatographed on a column of silica (0.02–0.045 mm) 4 cm in diameter, eluted with a dichloromethane/ethyl acetate mixture (4:1 by volume). The fractions containing the product are concentrated under reduced pressure (2.7 kPa) at 40° C. 1 g of 2,6-bis-(2', 2'-dimethyl-1', 3'-dioxolan-4'-ylmethyloxymethyl)-pyridine is thus obtained.

(S)-(+)-2,2-Dimethyl-1,3-dioxolane-4-methanol can be prepared according to Baer, J. Biol. Chem. 128, 463 (1939).

2,6-Bis(chloromethyl)pyridine can be prepared according to W. Baker, J. Chem. Soc., 3594 (1958).

EXAMPLE 22

A solution of 1.78 g of 2,6-dichloromethylpyridine, 2.34 g of 2-amino-1,3-propanediol and 2.8 cm$^3$ of triethylamine in 50 cm$^3$ of toluene is heated for 9 hours at a temperature in the region of the reflux temperature. The reaction mixture is cooled to 20° C. and is then concentrated under reduced pressure (2.7 kPa) at 40° C. The oily residue (4 g) is chromatographed on a column of silica (0.02–0.045 mm) 4 cm in diameter, eluted with a chloroform/methanol/20% aqueous ammonia mixture (12:6:1 by volume). The fractions containing the product are concentrated under reduced pressure (2.7 kPa) at 40° C. The yellow oil obtained (0.5 g) is dissolved in 15 cm$^3$ of distilled water and the solution is filtered. The filtrate is freeze-dried (−36° C. to +25° C. over 16 h at 2.7 kPa). 120 mg of N,N'-(1,3-dihydroxy-2-propyl)pyridine-2,6-dimethanamine are thus obtained in the form of a resin. [$^1$H NMR spectrum (400 MHz, (CD$_3$)$_2$SO-d$_6$, δ in ppm): 2.62 (mt, 2H: 2×NCH); 3.38 and 3.45 (2dd, J=11 and 6 Hz, 8H: 4×CH$_2$O); 3.89 (limiting AB, 4H: 2×ArCH$_2$N); from 4.30 to 4.70 (broad unres. mult.: 4×OH); 7.31 (d, J=8 Hz, 2H: =CH at 3 and =CH at 5); 7.71 (t, J=8 Hz, 1H: =CH at 4)].

EXAMPLE 23

A solution of 4.15 g of 2,5-diaminopyridine hydrochloride and 12.82 cm$^3$ of triethylamine in 100 cm$^3$ of tetrahydrofuran is stirred for 30 minutes at 20° C. A solution of 5.59 g of 3-methoxypropanoyl chloride in 30 cm$^3$ of tetrahydrofuran is added over 20 minutes and the reaction mixture is then stirred for 12 hours at 20° C. The mixture is concentrated under reduced pressure (2.7 kPa) at 40° C. The pasty residue is taken up in 100 cm$^3$ of acetone. The solid formed is filtered off and rinsed with 300 cm$^3$ in total of acetone. The filtrates are combined and concentrated under reduced pressure (2.7 kPa) at 50° C. to give a brown oil (1.8 g) which is purified by chromatography on a column of silica (0.020–0.045 mm) eluted with a dichloromethane/methanol mixture (19:1 by volume) for the first 50 fractions and a dichloromethane/methanol mixture (9:1 by volume) for the following fractions, collecting 60 cm$^3$ fractions. The fractions containing the expected product are combined and concentrated under reduced pressure (2.7 kPa) at 50° C. The yellow oil is dissolved in 25 cm$^3$ of ethanol. 100 cm$^3$ of isopropyl ether are added to this solution and the mixture is stirred for 24 hours at 20° C. The solid formed is filtered off and then rinsed with 30 cm$^3$ in total of isopropyl ether, then dried to constant weight to give 0.35 g of 2,5-bis-N,N'-(3-methoxy-1-propylamido)pyridine in the form of a beige-coloured solid melting at 124° C. [$^1$H NMR spectrum (400 MHz, (CD$_3$)$_2$SO-d$_6$, δ in ppm): 2.57 and 2.62 (2 t, J=6 Hz, 2H each: COCH$_2$); 3.24 and 3.26 (2 s, 3H each: OCH$_3$); 3.62 (mt, 4H: 2×OCH$_2$); 7.94 (dd, J=9 and 2.5 Hz, 1H: H4 of the pyridine); 8.03 (d, J=9 Hz, 1H: H3 of the pyridine); 8.56 (d, J=2.5 Hz, 1H: H6 of the pyridine); 10.09 and 10.41 (2 s, 1H each: CONH).

EXAMPLE 24

6.91 g of potassium carbonate and 8.75 g of tetrabutylammonium hydrogensulphate are successively added to a solution of 7.1 g of 2,6-pyridinedimethanol in 100 cm$^3$ of tetrahydrofuran. The reaction mixture is cooled to 20° C. in an ice bath and 6.60 g of potassium hydroxide are then added, while maintaining the temperature of the reaction mixture at 30° C. After stirring for 15 minutes at this temperature, a solution of 4.73 cm$^3$ of 2-bromoethyl methyl ether in 10 cm$^3$ of tetrahydrofuran is added over approximately 15 minutes. The reaction mixture is stirred for 12 hours at 20° C. and a solution of 4.73 cm$^3$ of 2-bromoethyl methyl ether in 10 cm$^3$ of tetrahydrofuran is then added over 15 minutes. The reaction mixture is stirred for 48 hours at 20° C. The white suspension obtained is filtered. The solid is rinsed with 750 cm³ in total of tetrahydrofuran. The combined filtrates are concentrated under reduced pressure (2.7 kPa) at 40° C. The residual oil obtained (18 g) is purified by chromatography on a column of silica (0.020–0.045 mm), eluting with an ethyl acetate/methanol mixture (9:1 by volume), collecting 50 cm³ fractions). The fractions containing the expected product are combined and concentrated under reduced pressure (2.7 kPa) at 50° C. The oil obtained (1.6 g) is dissolved in 12 cm³ of distilled water and the solution is filtered. After freeze-drying, 1.52 g of 2,6-bis(2-methoxyethyloxymethyl)pyridine are obtained in the form of a fluid yellow oil [$^1$H NMR spectrum (400 MHz, (CD$_3$)$_2$SO-d$_6$, δ in ppm): 3.29 (s, 6H: 2×OCH$_3$); 3.53 and 3.66 (2 mts, 4H each: OCH$_2$CH$_2$O); 4.57 (s, 4H: 2×ArCH$_2$O); 7.35 (d, J=8 Hz, 2H: =CH at 3 and =CH at 5); 7.83 (t, J=8 Hz, 1H: =CH at 4)].

EXAMPLE 25

0.33 g of benzoyl peroxide and 13.30 g of N-chlorosuccinimide are added to a solution of 5.40 g of 2,5-dimethylpyrazine in 150 cm³ of carbon tetrachloride. The reaction mixture is heated for 24 hours at a temperature in the region of the reflux temperature and is then cooled to 20° C. and filtered. A solution of 7.32 g of N-methylglucamine in 60 cm³ of carbon tetrachloride is added to the solution obtained. The reaction mixture is heated at a temperature in the region of the reflux temperature for 4 hours and is then concentrated under reduced pressure (2.7 kPa) at 40° C. The residual oil (10 g) is purified by chromatography on a column of silica (0.020–0.045 mm), eluting with a chloroform/methanol/20% aqueous ammonia mixture (24:6:1 by volume) for the first 13 fractions and chloroform/methanol/20% aqueous ammonia (12:6:2 by volume) for the following fractions, collecting 100 cm³ fractions. The fractions containing the expected product are combined and concentrated under reduced pressure (2.7 kPa) at 50° C. The yellow oil obtained (1.3 g) is again purified by chromatography on a column of silica (0.020–0.045 mm), eluting with a chloroform/methanol/20% aqueous ammonia mixture (24:6:1 by volume), collecting 100 cm³ fractions. The fractions containing the expected product are combined and concentrated under reduced pressure (2.7 kPa) at 50° C. The yellow oil obtained (0.6 g) is crystallized from a methanol/methyl ethyl ketone/acetone mixture. The solid is filtered off and then dried to constant weight to give 0.10 g of N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dimethanamine in the form of a beige-coloured solid [$^1$H NMR spectrum (400 MHz, (CD$_3$)$_2$SO-d$_6$ with addition of a few drops of CD$_3$COOD-d$_4$, δ in ppm): 2.42 (broad s, 6H: NCH$_3$); 2.72 and 2.83 (2 dd, J=13 and 8 Hz and J=13 and 4 Hz respectively, 2H each: NCH$_2$); 3.40 and 3.59 (2 dd, J=11 and 5.5 Hz and J=11 and 2.5 Hz respectively, 2H each: OCH$_2$ at __); from 3.40 to 3.55 (mt, 4H: CH at ζ and CH at η); 3.67 (d, J=2.5 Hz, 2H: CH at ε); 3.88 (mt, 2H: CH at d); 3.99 (limiting AB, 4H: ArCH$_2$N); 8.71 (s, 2H: =CH)].

EXAMPLE 26

5 g of 2,2-bis(acetoxymethyl)propanoic acid chloride are added to a solution of 1.1 g of 2,6-diaminopyridine in 20 cm³ of toluene. The reaction mixture is stirred for 72 hours at 20° C. The yellow suspension obtained is filtered. The filtrate is concentrated under reduced pressure (2.7 kPa) at 40° C. The residual oil (3.46 g) is purified by chromatography on a column of silica (0.020–0.045 mm), eluting with a chloroform/methanol/20% aqueous ammonia mixture (12:6:1 by volume), collecting 10 cm³ fractions. The fractions containing the expected product are combined and concentrated under reduced pressure (2.7 kPa) at 40° C. The orange oil is taken up in 10 cm³ of distilled water and the solution is filtered. After freeze-drying, 0.230 g of 2,6-bis-N,N'-(1,3-dihydroxy-2-methylprop-2-ylamido)pyridine-2,6-bis-N,N'-(1,3-dihydroxy-2-methylprop-2-ylamido)pyridine is obtained in the form of a yellow oil [$^1$H NMR spectrum (300 MHz, (CD$_3$)$_2$SO-d$_6$, δ in ppm): 1.04 (s, 6H: 2×CH$_3$); 3.59 (s, 8H: 4×CH$_2$O); 5.00 to 5.45 (unres. mult., 4H: 4×OH); 7.78 (mt, 3H: aromatic H of the pyridine); 9.89 (s, 2H: 2×CONH)].

2,2-Bis(acetoxymethyl)propionic acid chloride can be prepared according to the method described by I. Henrik, J. Amer. Chem. Soc. 118, 6388–95 (1996).

The compounds of formula (I) have advantageous pharmacological properties. They are hypoglycaemiant agents.

The hypoglycaemiant activity of the compounds of formula (I) was determined on the hyperglycaemic response to the administration of glucose orally to normoglycaemic mice, according to the following procedure:

Swiss albino mice weighing between 22 and 26 g are fasted for 2 hours. At the end of this period, the glycaemia is measured and, immediately, a dose of glucose (2 g/kg) is administered orally. Thirty minutes later, the glycaemia is measured again. The mice which respond with a hyperglycaemia of greater than 170 mg/dl are selected and used to detect the hypoglycaemiant activity of the compounds according to the invention. The m such as water or a mixture of methylcellulose/tween and water or of the vehicle once a day by gastric intubation. The treatment lasts for 4 days. On the 4th day, after the final treatment, the animals receive a dose of glucose (2 g/kg) and the glycaemia is measured 20 to 40 minutes later. The percentage of inhibition of the hyperglycaemic response to the administration of glucose is calculated relative to the response measured in the group treated with the vehicle.

In this test, the compounds according to the invention have a percentage of inhibition of glycaemia of greater than or equal to 10%.

The compounds of general formula (I) according to the invention are of low toxicity. Their LD$_{50}$ is greater than 2000 mg/kg orally in mice.

In human therapy, these products are useful in the prevention and treatment of diabetes and in particular type II diabetes (NID diabetes), obesity-related diabetes, maturity-onset diabetes, metaplethoric diabetes, adult-onset diabetes and mild diabetes. They can be used as a complement to insulin therapy in insulin-dependent diabetes, in which they allow the dose of insulin to be reduced gradually, brittle diabetes, insulin-resistant diabetes, as a complement to hypoglycaemiant sulphamides when the latter do not bring about a sufficient lowering of glycaemia. These products can also be used in complications of diabetes such as hyperlipaemias, lipid metabolism disorders, dyslipaemias and obesity. They are also useful in the prevention and treatment of atherosclerosis lesions and their complications (coronopathies, myocardial infarction, cardiomyopathies, evolution of these three complications towards left ventricular insufficiency, various arteriopathies, arteritis of the lower limbs with claudication and evolution towards ulcers and gangrene, cerebrovascular insufficiency and its complications, sexual impotence of vascular origin), diabetic retinopathy and all its symptoms (increase in capillary permeability, capillary dilation and thrombosis, microaneurisms, arteriovenous shunt, venous dilation, punctiform and macular haemorrhage, exudates, macular oedemas, symptoms of proliferative retinopathy: neovascularization, proliferative retinitis scars, haemorrhage of the vitreous humour, detachment of the retina), diabetic cataracts, diabetic neuropathy in its various forms (peripheral polyneuropathies and their symptoms such as paraesthesia, hyperaesthesia and pain, mononeuropathies, radiculopathies, autonomic neuropathies, diabetic amyotrophy), diabetic symptoms on the feet (ulcers of the lower extremities and of the feet), diabetic nephropathy in its two forms—diffuse and nodular—atheromatosis (increase in HDL lipoproteins promoting the removal of cholesterol from atheroma plaques, lowering of LDL lipoproteins, lowering of the LDL/HDL ratio, inhibition of the oxidation of LDLs, decrease in platelet adhesiveness), hyperlipaemias and dyslipaemias (hypercholesterolaemias, hypertriglyceridaemias, normalization of the level of fatty acids, normalization of uricaemia, normalization of apoproteins A and B), cataracts, arterial hypertension and its consequences.

The medicaments according to the invention consist of a compound according to the invention or a combination of these products, in pure form or in the form of a composition in which it is combined with any other pharmaceutically compatible product, which can be inert or physiologically active. The medicaments according to the invention can be used orally, parenterally, rectally or topically.

Tablets, pills, powders (gelatin capsules or cachets) or granules can be used as solid compositions for oral administration. In these compositions, the active principle according to the invention is mixed with one or more inert diluents, such as starch, cellulose, sucrose, lactose or silica, under a stream of argon. These compositions can also comprise substances other than diluents, for example one or more lubricants such as magnesium stearate or talc, a dye, a coating (dragees) or a varnish.

Pharmaceutically acceptable solutions, suspensions, emulsions, syrups and elixirs containing inert diluents such as water, ethanol, glycerol, plant oils or liquid paraffin can be used as liquid compositions for oral administration. These compositions can comprise substances other than diluents, for example wetting, sweetening, thickening, flavouring or stabilizing products.

The sterile compositions for parenteral administration can preferably be aqueous or non-aqueous solutions, suspensions or emulsions. Water, propylene glycol, a polyethylene glycol, plant oils, in particular olive oil, injectable organic esters, for example ethyl oleate, or other suitable organic solvents can be used as solvent or vehicle. These compositions can also contain adjuvants, in particular wetting agents, tonicity agents, emulsifiers, dispersing agents and stabilizers. The sterilization can be carried out in several ways, for example by aseptic filtration, by incorporating sterilizing agents into the composition, by irradiation or by heating. They can also be prepared in the form of sterile solid compositions which can be dissolved, at the time of use, in sterile water or any other injectable sterile medium.

The compositions for rectal administration are suppositories or rectal capsules which contain, besides the active product, excipients such as cocoa butter, semisynthetic glycerides or polyethylene glycols.

The compositions for topical administration can be, for example, creams, lotions, eyedrops, mouth washes, nasal drops or aerosols.

The doses depend upon the desired effect, the duration of the treatment and the route of administration used; they are generally between 150 mg and 600 mg per day via the oral route for an adult, with unit doses ranging from 50 mg to 200 mg of active substance.

In general, the doctor will determine the appropriate dose as a function of the age, the weight and all the other personal factors of the individual to be treated.

The examples which follow illustrate compositions according to the invention:

Example A

Gelatin capsules containing a 50 mg dose of active product and having the following composition are prepared, according to the usual technique:

| | |
|---|---|
| Active product | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

Example B

Tablets containing a 50 mg dose of active product and having the following composition are prepared, according to the usual technique:

| | |
|---|---|
| Active product | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerol | | and titanium oxide (72/3.5/24.5), q.s. 1 finished film-coated tablet weighing 245 mg.

Example C

An injectable solution containing 50 mg of active product and having the following composition is prepared:

| | |
|---|---|
| Active product | 50 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water | qs 4 ml |

The invention also relates to the use of the compounds of general formula (I) for the preparation of pharmaceutical compositions which are useful for the treatment or prevention of diabetes and complications of diabetes.

What is claimed is:

1. A pharmaceutical composition comprising at least one compound of formula:

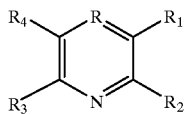

(I)

in which

R represents a nitrogen atom, $R_1$ and $R_3$ each represent the same radical selected from the group consisting of —CO—$NR_5R_6$, —CO—N(CH($CH_2OH)_2)_2$, —CO—N($CH_2OH)_2$, —CO—N($CH_2$—CH($CH_2OH)_2)_2$, —CO—N($CH_2$—(CHOH)$_n$—$CH_2OH)_2$ in which n is equal to 0, 1, 2, 3 or 4, —$NR_5$—CO—$R_6$, —$CH_2$—O—$R_6$, —$NR_5$—CO—$R_6$, —$CH_2$—$NR_5R_6$, —$CH_2$—N($CH_2OH)_2$, —$CH_2$—N($CH_2$—(CHOH)$_y$—$CH_2OH)_2$ in which y is equal to 0, 1, 2, 3 or 4, —$CH_2$—N(CH($CH_2OH)_2)_2$ and —$CH_2$—N($CH_2$—CH($CH_2OH)_2)_2$ and $R_2$ and $R_4$ each represent a hydrogen atom, $R_5$ represents a hydrogen atom or an alkyl radical, $R_6$ represents a radical —$CH_2$—(CHOH)m—$CH_2OH$ in which m is equal to 0, 1, 2, 3 or 4, -alk-O-alk-$CH_2OH$, - alk-O-alk, —CH($CH_2OH)_2$, —C($CH_2OH)_3$, —C($CH_3$)($CH_2OH)_2$, —$CH_2$—CH($CH_2OH)_2$ or —CH($CH_2OH$)—(CHOH)$_x$—$CH_2OH$ in which x is equal to 1, 2, 3 or 4, alk represents an alkyl radical, the alkyl radicals containing, unless otherwise stated, 1 to 6 carbon atoms in a straight or branched chain, stereoisomers thereof and salts thereof with an inorganic or organic acid.

2. A pharmaceutical composition according to claim 1, wherein said compound is selected from the group consisting of:

N,N'-bis(2-hydroxyethyl)pyrazine-2,5-dicarboxamide,
N,N'-bis(2-hydroxyethyl)pyrazine-2,6-dicarboxamide,
N-methyl-N-(2-hydroxyethyl-N'-methyl-N'(2-hydroxyethyl)pyrazine-2,5-dicarboxamide,
N-methyl-N-(2-hydroxyethyl)-N'-methyl-N'(2-hydroxyethyl)pyrazine-2,6-dicarboxamide,
N,N,N',N'-tetrakis(2-hydroxyethyl)pyrazine-2,5-dicarboxamide,
N,N,N',N'-tetrakis(2-hydroxyethyl)pyrazine-2,6-dicarboxamide,
N,N'-bis(2,3-dihydroxy-1-propyl)pyrazine-2,5-dicarboxamide,
N,N'-bis(2,3-dihydroxy-1-propyl)pyrazine-2,6-dicarboxamide,
N-methyl-N-(2,3-dihydroxy-1-propyl)-N'-methyl-N'-(2,3-dihydroxy-1-propyl)pyrazine-2,5-dicarboxamide,
N-methyl-N-(2,3-dihydroxy-1-propyl)-N'-methyl-N'-(2,3-dihydroxy-1-propyl)pyrazine-2,6-dicarboxamide,
N,N,N',N'-tetrakis(2,3-dihydroxy-1-propyl)pyrazine-2,5-dicarboxamide,
N,N,N',N'-tetrakis(2,3-dihydroxy-1-propyl)pyrazine-2,6-dicarboxamide,
N,N'-bis(1,3-dihydroxy-2-propyl)pyrazine-2,5-dicarboxamide,
N,N'-bis(1,3-dihydroxy-2-propyl)pyrazine-2,6-dicarboxamide,
N-methyl-N-(1,3-dihydroxy-2-propyl)-N'-methyl-N'-(1,3-dihydroxy-2-propyl)pyrazine-2,5-dicarboxamide,
N-methyl-N-(1,3-dihydroxy-2-propyl)-N'-methyl-N'-(1,3-dihydroxy-2-propyl)pyrazine-2,6-dicarboxamide,
N,N,N',N'-tetrakis(1,3-dihydroxy-2-propyl)pyrazine-2,5-dicarboxamide,
N,N,N',N'-tetrakis(1,3-dihydroxy-2-propyl)pyrazine-2,6-dicarboxamide,
N,N'-bis(2,3,4-trihydroxy-1-butyl)pyrazine-2,5-dicarboxamide,
N,N'-bis(2,3,4-trihydroxy-1-butyl)pyrazine-2,6-dicarboxamide,
N-methyl-N-(2,3,4-trihydroxy-1-butyl)-N'-methyl-N'-(2,3,4-trihydroxy-1-butyl)pyrazine-2,5-dicarboxamide,
N-methyl-N-(2,3,4-trihydroxy-1-butyl)-N'-methyl-N'-(2,3,4-trihydroxy-1-butyl)pyrazine-2,6-dicarboxamide,
N,N'-bis(1,3,4-trihydroxy-2-butyl)pyrazine-2,5-dicarboxamide,
N,N'-bis(1,3,4-trihydroxy-2-butyl)pyrazine-2,6-dicarboxamide,
N-methyl-N-(1,3,4-trihydroxy-2-butyl)-N'-methyl-N'-(1,3,4-trihydroxy-2-butyl)pyrazine-2,5-dicarboxamide,
N-methyl-N-(1,3,4-trihydroxy-2-butyl)-N'-methyl-N'-(1,3,4-trihydroxy-2-butyl)pyrazine-2,6-dicarboxamide,
N,N'-bis[2-(hydroxymethyl)-3-hydroxy-1-propyl]-pyrazine-2,5-dicarboxamide,
N,N'-bis[2-(hydroxymethyl)-3-hydroxy-1-propyl]-pyrazine-2,6-dicarboxamide,
N-methyl-N-[2-(hydroxymethyl)-3-hydroxy-1-propyl]-N'-methyl-N'-[2-(hydroxymethyl)-3-hydroxy-1-propyl]-pyrazine-2,5-dicarboxamide,
N-methyl-N-[2-(hydroxymethyl)-3-hydroxy-1-propyl]-N'-methyl-N'-[2-(hydroxymethyl)-3-hydroxy-1-propyl]-pyrazine-2,6-dicarboxamide,
N,N,N',N'-tetrakis[2-(hydroxymethyl)-3-hydroxy-1-propyl]pyrazine-2,5-dicarboxamide,
N,N,N',N'-tetrakis[2-(hydroxymethyl)-3-hydroxy-1-propyl]pyrazine-2,6-dicarboxamide,
N,N'-bis[1,1,1-tri(hydroxymethyl)methyl]pyrazine-2,5-dicarboxamide,
N,N'-bis[1,1,1-tri(hydroxymethyl)methyl]pyrazine-2,6-dicarboxamide,
N-methyl-N-[1,1,1-tri(hydroxymethyl)methyl]-N'-methyl-N'-[1,1,1-tri(hydroxymethyl)methyl]pyrazine-2,5-dicarboxamide,
N-methyl-N-[1,1,1-tri(hydroxymethyl)methyl]-N'-methyl-N'-[1,1,1-tri(hydroxymethyl)methyl]pyrazine-2,6-dicarboxamide,
N,N'-bis[1,1-di(hydroxymethyl)-1-ethyl]pyrazine-2,5-dicarboxamide,
N,N'-bis[1,1-di(hydroxymethyl)-1-ethyl]pyrazine-2,6-dicarboxamide,
N-methyl-N-[1,1-di(hydroxymethyl)-1-ethyl]-N'-methyl-N'-[1,1-di(hydroxymethyl)-1-ethyl]pyrazine-2,5-dicarboxamide,
N-methyl-N-[1,1-di(hydroxymethyl)-1-ethyl]-N'-methyl-N'-[1,1-di(hydroxymethyl)-1-ethyl]pyrazine-2,6-dicarboxamide,
N,N'-bis(2-hydroxyethyl)pyridine-2,5-dicarboxamide,
N,N'-bis(2-hydroxyethyl)pyridine-2,6-dicarboxamide,
N,N'-bis(2-hydroxyethyl)pyridine-3,5-dicarboxamide,
N-methyl-N-(2-hydroxyethyl)-N'-methyl-N'-(2-hydroxyethyl)pyridine-2,5-dicarboxamide,
N-methyl-N-(2-hydroxyethyl)-N'-methyl-N'-(2-hydroxyethyl)pyridine-2,6-dicarboxamide,
N-methyl-N-(2-hydroxyethyl)-N'-methyl-N'-(2-hydroxyethyl)pyridine-3,5-dicarboxamide,
N,N,N',N'-tetrakis(2-hydroxyethyl)pyridine-2,5-dicarboxamide,
N,N,N',N'-tetrakis(2-hydroxyethyl)pyridine-2,6-dicarboxamide,
N,N,N',N'-tetrakis(2-hydroxyethyl)pyridine-3,5-dicarboxamide, N,N'-bis(2,3-dihydroxy-1-propyl)pyridine-2,5-dicarboxamide,
N,N'-bis(2,3-dihydroxy-1-propyl)pyridine-2,6-dicarboxamide,
N,N'-bis(2,3-dihydroxy-1-propyl)pyridine-3,5-dicarboxamide,
N-methyl-N-(2,3-dihydroxy-1-propyl)-N'-methyl-N'-(2,3-dihydroxy-1-propyl)pyridine-2,5-dicarboxamide,
N-methyl-N-(2,3-dihydroxy-1-propyl)-N'-methyl-N'-(2,3-dihydroxy-1-propyl)pyridine-2,6-dicarboxamide,
N-methyl-N-(2,3-dihydroxy-1-propyl)-N'-methyl-N'-(2,3-dihydroxy-1-propyl)pyridine-3,5-dicarboxamide,
N,N,N',N'-tetrakis(2,3-dihydroxy-1-propyl)pyridine-2,5-dicarboxamide,
N,N,N',N'-tetrakis(2,3-dihydroxy-1-propyl)pyridine-2,6-dicarboxamide,
N,N,N',N'-tetrakis(2,3-dihydroxy-1-propyl)pyridine-3,5-dicarboxamide,
N,N'-bis(1,3-dihydroxy-2-propyl)pyridine-2,5-dicarboxamide,
N,N'-bis(1,3-dihydroxy-2-propyl)pyridine-2,6-dicarboxamide,
N,N'-bis(1,3-dihydroxy-2-propyl)pyridine-3,5-dicarboxamide,
N-methyl-N-(1,3-dihydroxy-2-propyl)-N'-methyl-N'-(1,3-dihydroxy-2-propyl)pyridine-2,5-dicarboxamide,
N-methyl-N-(1,3-dihydroxy-2-propyl)-N'-methyl-N'-(1,3-dihydroxy-2-propyl)pyridine-2,6-dicarboxamide,
N-methyl-N-(1,3-dihydroxy-2-propyl)-N'-methyl-N'-(1,3-dihydroxy-2-propyl)pyridine-3,5-dicarboxamide,
N,N,N',N'-tetrakis(1,3-dihydroxy-2-propyl)pyrazine-2,5-dicarboxamide,
N,N,N',N'-tetrakis(1,3-dihydroxy-2-propyl)pyrazine-2,6-dicarboxamide,
N,N'-bis(2,3,4-trihydroxy-1-butyl)pyridine-2,5-dicarboxamide,
N,N'-bis(2,3,4-trihydroxy-1-butyl)pyridine-2,6-dicarboxamide,
N,N'-bis(2,3,4-trihydroxy-1-butyl)pyridine-3,5-dicarboxamide,
N-methyl-N-(2,3,4-trihydroxy-1-butyl)-N'-methyl-N'-(2,3,4-trihydroxy-1-butyl)pyridine-2,5-dicarboxamide,
N-methyl-N-(2,3,4-trihydroxy-1-butyl)-N'-methyl-N'-(2,3,4-trihydroxy-1-butyl)pyridine-2,6-dicarboxamide,
N-methyl-N-(2,3,4-trihydroxy-1-butyl)-N'-methyl-N'-(2,3,4-trihydroxy-1-butyl)pyridine-3,5-dicarboxamide,
N,N'-bis(1,3,4-trihydroxy-2-butyl)pyridine-2,5-dicarboxamide,
N,N'-bis(1,3,4-trihydroxy-2-butyl)pyridine-2,6-dicarboxamide,
N,N'-bis(1,3,4-trihydroxy-2-butyl)pyridine-3,5-dicarboxamide,
N-methyl-N-(1,3,4-trihydroxy-2-butyl)-N'-methyl-N'-(1,3,4-trihydroxy-2-butyl)pyridine-2,5-dicarboxamide,
N-methyl-N-(1,3,4-trihydroxy-2-butyl)-N'-methyl-N'-(1,3,4-trihydroxy-2-butyl)pyridine-2,6-dicarboxamide,
N-methyl-N-(1,3,4-trihydroxy-2-butyl)-N'-methyl-N'-(1,3,4-trihydroxy-2-butyl)pyridine-3,5-dicarboxamide,
N,N'-bis[2-(hydroxymethyl)-3-hydroxy-1-propyl]-pyridine-2,5-dicarboxamide,
N,N'-bis[2-(hydroxymethyl)-3-hydroxy-1-propyl]-pyridine-2,6-dicarboxamide,
N,N'-bis[2-(hydroxymethyl)-3-hydroxy-1-propyl]-pyridine-3,5-dicarboxamide,
N-methyl-N-[2-(hydroxymethyl)-3-hydroxy-1-propyl]-N'-methyl-N'-[2-(hydroxymethyl)-3-hydroxy-1-propyl]-pyridine-2,5-dicarboxamide,
N-methyl-N-[2-(hydroxymethyl)-3-hydroxy-1-propyl]-N'-methyl-N'-[2-(hydroxymethyl)-3-hydroxy-1-propyl]-pyridine-2,6-dicarboxamide,
N-methyl-N-[2-(hydroxymethyl)-3-hydroxy-1-propyl]-N'-methyl-N'-[2-(hydroxymethyl)-3-hydroxy-1-propyl]-pyridine-3,5-dicarboxamide,
N,N,N',N'-tetrakis[2-(hydroxymethyl)-3-hydroxy-1-propyl]pyridine-2,5-dicarboxamide,
N,N,N',N'-tetrakis[2-(hydroxymethyl)-3-hydroxy-1-propyl]pyridine-2,6-dicarboxamide,
N,N,N',N'-tetrakis[2-(hydroxymethyl)-3-hydroxy-1-propyl]pyridine-3,5-dicarboxamide,
N,N'-bis[1,1,1-tri(hydroxymethyl)methyl]pyridine-2,5-dicarboxamide,
N,N'-bis[1,1,1-tri(hydroxymethyl)methyl]pyridine-2,6-dicarboxamide,
N,N'-bis[1,1,1-tri(hydroxymethyl)methyl]pyridine-3,5-dicarboxamide,
N-methyl-N-[1,1,1-tri(hydroxymethyl)methyl]-N'-methyl-N'-[1,1,1-tri(hydroxymethyl)methyl]pyridine-2,5-dicarboxamide,
N-methyl-N-[1,1,1-tri(hydroxymethyl)methyl]-N'-methyl-N'-[1,1,1-tri(hydroxymethyl)methyl]pyridine-2,6-dicarboxamide,
N-methyl-N-[1,1,1-tri(hydroxymethyl)methyl]-N'-methyl-N'-[1,1,1-tri(hydroxymethyl)methyl]pyridine-3,5-dicarboxamide,
N,N'-bis[1,1-di(hydroxymethyl)-1-ethyl]pyridine-2,5-dicarboxamide,
N,N'-bis[1,1-di(hydroxymethyl)-1-ethyl]pyridine-2,6-dicarboxamide,
N,N'-bis[1,1-di(hydroxymethyl)-1-ethyl]pyridine-3,5-dicarboxamide,
N-methyl-N-[1,1-di(hydroxymethyl)-1-ethyl]-N'-methyl-N'-[1,1-di(hydroxymethyl)-1-ethyl]pyridine-2,5-dicarboxamide,
N-methyl-N-[1,1-di(hydroxymethyl)-1-ethyl]-N'-methyl-N'-[1,1-di(hydroxymethyl)-1-ethyl]pyridine-2,6-dicarboxamide,
N-methyl-N-[1,1-di(hydroxymethyl)-1-ethyl]-N'-methyl-N'-[1,1-di(hydroxymethyl)-1-ethyl]pyridine-3,5-dicarboxamide,
N,N'-bis(2-hydroxyethyl)pyrazine-2,5-dimethanamine,
N,N'-bis(2-hydroxyethyl)pyrazine-2,6-dimethanamine,
N-methyl-N-(2-hydroxyethyl)-N'-methyl-N'-(2-hydroxyethyl)pyrazine-2,5-dimethanamine,
N-methyl-N-(2-hydroxyethyl)-N'-methyl-N'-(2-hydroxyethyl)pyrazine-2,6-dimethanamine,
N,N,N',N'-tetrakis(2-hydroxyethyl)pyrazine-2,5-dimethanamine,
N,N,N',N'-tetrakis(2-hydroxyethyl)pyrazine-2,6-dimethanamine,
N,N'-bis(2,3-dihydroxy-1-propyl)pyrazine-2,5-dimethanamine,
N,N'-bis(2,3-dihydroxy-1-propyl)pyrazine-2,6-dimethanamine,
N-methyl-N-(2,3-dihydroxy-1-propyl)-N'-methyl-N'-(2,3-dihydroxy-1-propyl)pyrazine-2,5-dimethanamine,
N-methyl-N-(2,3-dihydroxy-1-propyl)-N'-methyl-N'-(2,3-dihydroxy-1-propyl)pyrazine-2,6-dimethanamine,
N,N,N',N'-tetrakis(2,3-dihydroxy-1-propyl)pyrazine-2,5-dimethanamine,
N,N,N',N'-tetrakis(2,3-dihydroxy-1-propyl)pyrazine-2,6-dimethanamine,
N,N'-bis(1,3-dihydroxy-2-propyl)pyrazine-2,5-dimethanamine,
N,N'-bis(1,3-dihydroxy-2-propyl)pyrazine-2,6-dimethanamine, N-methyl-N-(1,3-dihydroxy-2-propyl)-N'-methyl-N'-(1,3-dihydroxy-2-propyl)pyrazine-2,5-dimethanamine,
N-methyl-N-(1,3-dihydroxy-2-propyl)-N'-methyl-N'-(1,3-dihydroxy-2-propyl)pyrazine-2,6-dimethanamine,
N,N,N',N'-tetrakis(1,3-dihydroxy-2-propyl)pyrazine-2,5-dimethanamine,
N,N,N',N'-tetrakis(1,3-dihydroxy-2-propyl)pyrazine-2,6-dimethanamine,
N,N'-bis(2,3,4-trihydroxy-1-butyl)pyrazine-2,5-dimethanamine,
N,N'-bis(2,3,4-trihydroxy-1-butyl)pyrazine-2,6-dimethanamine,
N-methyl-N-(2,3,4-trihydroxy-1-butyl)-N'-methyl-N'-(2,3,4-trihydroxy-1-butyl)pyrazine-2,5-dimethanamine,
N-methyl-N-(2,3,4-trihydroxy-1-butyl)-N'-methyl-N'-(2,3,4-trihydroxy-1-butyl)pyrazine-2,6-dimethanamine,
N,N'-bis(1,3,4-trihydroxy-2-butyl)pyrazine-2,5-dimethanamine,
N,N'-bis(1,3,4-trihydroxy-2-butyl)pyrazine-2,6-dimethanamine,
N-methyl-N-(1,3,4-trihydroxy-2-butyl)-N'-methyl-N'-(1,3,4-trihydroxy-2-butyl)pyrazine-2,5-dimethanamine,
N-methyl-N-(1,3,4-trihydroxy-2-butyl)-N'-methyl-N'-(1,3,4-trihydroxy-2-butyl)pyrazine-2,6-dimethanamine,
N,N'-bis[2-(hydroxymethyl)-3-hydroxy-1-propyl]-pyrazine-2,5-dimethanamine,
N,N'-bis[2-(hydroxymethyl)-3-hydroxy-1-propyl]-pyrazine-2,6-dimethanamine,
N-methyl-N-[2-(hydroxymethyl)-3-hydroxy-1-propyl]-N'-methyl-N'[2-(hydroxymethyl)-3-hydroxy-1-propyl]-pyrazine-2,5-dimethanamine,
N-methyl-N-[2-(hydroxymethyl)-3-hydroxy-1-propyl]-N'-methyl-N'-[2-(hydroxymethyl)-3-hydroxy-1-propyl]-pyrazine-2,6-dimethanamine,
N,N,N',N'-tetrakis[2-(hydroxymethyl)-3-hydroxy-1-propyl]pyrazine-2,5-dimethanamine,
N,N,N',N'-tetrakis[2-(hydroxymethyl)-3-hydroxy-1-propyl]pyrazine-2,6-dimethanamine,
N,N'-bis[1,1,1-tri(hydroxymethyl)methyl]pyrazine-2,5-dimethanamine,
N,N'-bis[1,1,1-tri(hydroxymethyl)methyl]pyrazine-2,6-dimethanamine,
N-methyl-N-[1,1,1-tri(hydroxymethyl)methyl]-N'-methyl-N'-[1,1,1-tri(hydroxymethyl)methyl]pyrazine-2,5-dimethanamine,
N-methyl-N-[1,1,1-tri(hydroxymethyl)methyl]-N'-methyl-N'-[1,1,1tri(hydroxymethyl)methyl]pyrazine-2,6-dimethanamine,
N,N'-bis[1,1-di(hydroxymethyl)-1-ethyl]pyrazine-2,5-dimethanamine,
N,N'-bis[1,1-di(hydroxymethyl)-1-ethyl]pyrazine-2,6-dimethanamine,
N-methyl-N-[1,1-di(hydroxymethyl)-1-ethyl]-N'-methyl-N'-[1,1-di(hydroxymethyl)-1-ethyl]pyrazine-2,5-dimethanamine,
N-methyl-N-[1,1-di(hydroxymethyl)-1-ethyl]-N'-methyl-N'-[1,1-di(hydroxymethyl)-1-ethyl]pyrazine-2,6-dimethanamine,
N,N'-bis(2-hydroxyethyl)pyridine-2,5-dimethanamine,
N,N'-bis(2-hydroxyethyl)pyridine-2,6-dimethanamine,
N,N'-bis(2-hydroxyethyl)pyridine-3,5-dimethanamine,
N-methyl-N-(2-hydroxyethyl)-N'-methyl-N'-(2-hydroxyethyl)pyridine-2,5-dimethanamine,
N-methyl-N-(2-hydroxyethyl)-N'-methyl-N'-(2-hydroxyethyl)pyridine-2,6-dimethanamine,
N-methyl-N-(2-hydroxyethyl)-N'-methyl-N'-(2-hydroxyethyl)pyridine-3,5-dimethanamine,
N,N,N',N'-tetrakis(2-hydroxyethyl)pyridine-2,5-dimethanamine,
N,N,N',N'-tetrakis(2-hydroxyethyl)pyridine-2,6-dimethanamine,
N,N,N',N'-tetrakis(2-hydroxyethyl)pyridine-3,5-dimethanamine,
N,N'-bis(2,3-dihydroxy-1-propyl)pyridine-2,5-dimethanamine,
N,N'-bis(2,3-dihydroxy-1-propyl)pyridine-2,6-dimethanamine,
N,N'-bis(2,3-dihydroxy-1-propyl)pyridine-3,5-dimethanamine,
N-methyl-N-(2,3-dihydroxy-1-propyl)-N'-methyl-N'-(2,3-dihydroxy-1-propyl)pyridine-2,5-dimethanamine,
N-methyl-N-(2,3-dihydroxy-1-propyl)-N'-methyl-N'-(2,3-dihydroxy-1-propyl)pyridine-2,6-dimethanamine,
N-methyl-N-(2,3-dihydroxy-1-propyl)-N'-methyl-N'-(2,3-dihydroxy-1-propyl)pyridine-3,5-dimethanamine,
N,N,N',N'-tetrakis(2,3-dihydroxy-1-propyl)pyridine-2,5-dimethanamine,
N,N,N',N'-tetrakis(2,3-dihydroxy-1-propyl)pyridine-2,6-dimethanamine,
N,N,N',N'-tetrakis(2,3-dihydroxy-1-propyl)pyridine-3,5-dimethanamine,
N,N'-bis(1,3-dihydroxy-2-propyl)pyridine-2,5-dimethanamine,
N,N'-bis(1,3-dihydroxy-2-propyl)pyridine-2,6-dimethanamine,
N,N'-bis(1,3-dihydroxy-2-propyl)pyridine-3,5-dimahanamine,
N-methyl-N-(1,3-dihydroxy-2-propyl)-N'-methyl-N'-(1,3-dihydroxy-2-propyl)pyridine-2,5-dimethanamine,
N-methyl-N-(1,3-dihydroxy-2-propyl)-N'-methyl-N'-(1,3-dihydroxy-2-propyl)pyridine-2,6-dimethanamine,
N-methyl-N-(1,3-dihydroxy-2-propyl)-N'-methyl-N'-(1,3-dihydroxy-2-propyl)pyridine-3,5-dimethanamine,
N,N,N',N'-tetrakis(1,3-dihydroxy-2-propyl)pyridine-2,5-dimethanamine,
N,N,N',N'-tetrakis(1,3-dihydroxy-2-propyl)pyridine-2,6-dimethanamine,
N,N,N',N'-tetrakis(1,3-dihydroxy-2-propyl)pyridine-3,5-dimethanamine,
N,N'-bis(2,3,4-trihydroxy-1-butyl)pyridine-2,5-dimethanamine,
N,N'-bis(2,3,4-trihydroxy-1-butyl)pyridine-2,6-dimethanamine,
N,N'-bis(2,3,4-trihydroxy-1-butyl)pyridine-3,5-dimethanamine,
N-methyl-N-(2,3,4-trihydroxy-1-butyl)-N'-methyl-N'-(2,3,4-trihydroxy-1-butyl)pyridine-2,5-dimethanamine,
N-methyl-N-(2,3,4-trihydroxy-1-butyl)-N'-methyl-N'-(2,3,4-trihydroxy-1-butyl)pyridine-2,6-dimethanamine,
N-methyl-N-(2,3,4-trihydroxy-1-butyl)-N'-methyl-N'-(2,3,4-trihydroxy-1-butyl)pyridine-3,5-dimethanamine,
N,N'-bis(1,3,4-trihydroxy-2-butyl)pyridine-2,5-dimethanamine,
N,N'-bis(1,3,4-trihydroxy-2-butyl)pyridine-2,6-dimethanamine,
N,N'-bis(1,3,4-trihydroxy-2-butyl)pyridine-3,5-dimethanamine,
N-methyl-N-(1,3,4-trihydroxy-2-butyl)-N'-methyl-N'-(1,3,4-trihydroxy-2-butyl)pyridine-2,5-dimethanamine,
N-methyl-N-(1,3,4-trihydroxy-2-butyl)-N'-methyl-N'-(1,3,4-trihydroxy-2-butyl)pyridine-2,6-dimethanamine,
N-methyl-N-(1,3,4-trihydroxy-2-butyl)-N'-methyl-N'-(1,3,4-trihydroxy-2-butyl)pyridine-3,5-dimethanamine,
N,N'-bis[2-(hydroxymethyl)-3-hydroxy-1-propyl]-pyridine-2,5-dimethanamine, N,N'-bis[2-(hydroxymethyl)-3-hydroxy-1-propyl]-pyridine-2,6-dimethanamine,
N,N'-bis[2-(hydroxymethyl)-3-hydroxy-1-propyl]-pyridine-3,5-dimethanamine,
N-methyl-N-[2-(hydroxymethyl)-3-hydroxy-1-propyl]-N'-methyl-N'-[2-(hydroxymethyl)-3-hydroxy-1-propyl]-pyridine-2,5-dimethanamine,
N-methyl-N-[2-(hydroxymethyl)-3-hydroxy-1-propyl]-N'-methyl-N'-[2-(hydroxymethyl)-3-hydroxy-1-propyl]-pyridine-2,6-dimethanamine,
N-methyl-N-[2-(hydroxymethyl)-3-hydroxy-1-propyl]-N'-methyl-N'-[2-(hydroxymethyl)-3-hydroxy-1-propyl]-pyridine-3,5-dimethanamine,
N,N,N',N'-tetrakis[2-(hydroxymethyl)-3-hydroxy-1-propyl]pyridine-2,5-dimethanamine,
N,N,N',N'-tetrakis[2-(hydroxymethyl)-3-hydroxy-1-propyl]pyridine-2,6-dimethanamine,
N,N,N',N'-tetrakis[2-(hydroxymethyl)-3-hydroxy-1-propyl]pyridine-3,5-dimethanamine,
N,N'-bis[1,1,1-tri(hydroxymethyl)methyl]pyridine-2,5-dimethanamine,
N,N'-bis[1,1,1-tri(hydroxymethyl)methyl]pyridine-2,6-dimethanamine,
N,N'-bis[1,1,1-tri(hydroxymethyl)methyl]pyridine-3,5-dimethanamine,
N-methyl-N-[1,1,1-tri(hydroxymethyl)methyl]-N'-methyl-N'-[1,1,1-tri(hydroxymethyl)methyl]pyridine-2,5-dimethanamine,
N-methyl-N-[1,1,1-tri(hydroxymethyl)methyl]-N'-methyl-N'-[1,1,1-tri(hydroxymethyl)methyl]pyridine-2,6-dimethanamine,
N-methyl-N-[1,1,1-tri(hydroxymethyl)methyl]-N'-methyl-N'-[1,1,1-tri(hydroxymethyl)methyl]pyridine-3,5-dimethanamine,
N,N'-bis[1,1-di(hydroxymethyl)-1-ethyl]pyridine-2,5-dimethanamine,
N,N'-bis[1,1-di(hydroxymethyl)-1-ethyl]pyridine-2,6-dimethanamine,
N,N'-bis[1,1-di(hydroxymethyl)-1-ethyl]pyridine-3,5-dimethanamine,
N-methyl-N-[1,1-di(hydroxymethyl)-1-ethyl]-N'-methyl-N'-[1,1-di(hydroxymethyl)-1-ethyl]pyridine-2,5-dimethanamine,
N-methyl-N-[1,1-di(hydroxymethyl)-1-ethyl]-N'-methyl-N'-[1,1-di(hydroxymethyl)-1-ethyl]pyridine-2,6-dimethanamine,
N-methyl-N-[1,1-di(hydroxymethyl)-1-ethyl]-N'-methyl-N'-[1,1-di(hydroxymethyl)-1-ethyl]pyridine-3,5-dimethanamine,
2,5-bis(2-hydroxyethyloxymethyl)pyrazine,
2,6-bis(2-hydroxyethyloxymethyl)pyrazine,
2,5-bis[(2R)-2,3-dihydroxy-1-propyloxymethyl]pyrazine,
2,5-bis[(2S)-2,3-dihydroxy-1-propyloxymethyl]pyrazine,
2,6-bis[(2R)-2,3-dihydroxy-1-propyloxymethyl]pyrazine,
2,6-bis[(2S)-2,3-dihydroxy-1-propyloxymethyl]pyrazine,
2,5-bis(1,3-dihydroxy-2-propyloxymethyl)pyrazine,
2,6-bis(1,3-dihydroxy-2-propyloxymethyl)pyrazine,
2,5-bis(2,3,4-trihydroxy-1-butyloxymethyl)pyrazine,
2,6-bis(2,3,4-trihydroxy-1-butyloxymethyl)pyrazine,
2,5-bis(1,3,4-trihydroxy-2-butyloxymethyl)pyrazine,
2,6-bis(1,3,4-trihydroxy-2-butyloxymethyl)pyrazine,
2,5-bis[2-(hydroxymethyl)-3-hydroxy-1-propyloxymethyl]pyrazine,
2,6-bis[2-(hydroxymethyl)-3-hydroxy-1-propyloxymethyl]pyrazine,
2,5-bis[1,1,1-tri(hydroxymethyl)methyloxymethyl]-pyrazine,
2,6-bis[1,1,1-tri(hydroxymethyl)methyloxymethyl]-pyrazine,
2,5-bis[1,1-di(hydroxymethyl)-1-ethyloxymethyl]-pyrazine,
2,6-bis[1,1-di(hydroxymethyl)-1-ethyloxymethyl]-pyrazine,
2,5-bis(2-hydroxyethyloxymethyl)pyridine,
2,6-bis(2-hydroxyethyloxymethyl)pyridine,
3,5-bis(2-hydroxyethyloxymethyl)pyridine,
2,5-bis(2,3-dihydroxy-1-propyloxymethyl)pyridine,
2,6-bis(2,3-dihydroxy-1-propyloxymethyl)pyridine,
3,5-bis(2,3-dihydroxy-1-propyloxymethyl)pyridine,
2,5-bis(1,3-dihydroxy-2-propyloxymethyl)pyridine,
2,6-bis(1,3-dihydroxy-2-propyloxymethyl)pyridine,
3,5-bis(1,3-dihydroxy-2-propyloxymethyl)pyridine,
2,5-bis(2,3,4-trihydroxy-1-butyloxymethyl)pyridine,
2,6-bis(2,3,4-trihydroxy-1-butyloxymethyl)pyridine,
3,5-bis(2,3,4-trihydroxy-1-butyloxymethyl)pyridine,
2,5-bis(1,3,4-trihydroxy-2-butyloxymethyl)pyridine,
2,6-bis(1,3,4-trihydroxy-2-butyloxymethyl)pyridine,
3,5-bis(1,3,4-trihydroxy-2-butyloxymethyl)pyridine,
2,5-bis[2-(hydroxymethyl)-3-hydroxy-1-propyloxymethyl]pyridine,
2,6-bis[2-(hydroxymethyl)-3-hydroxy-1-propyloxymethyl]pyridine,
3,5-bis,[2-(hydroxymethyl)-3-hydroxy-1-propyloxymethyl]pyridine,
2,5-bis[1,1,1-tri(hydroxymethyl)methyloxymethyl]-pyridine,
2,6-bis[1,1,1-tri(hydroxymethyl)methyloxymethyl]-pyridine,
3,5-bis[1,1,1-tri(hydroxymethyl)methyloxymethyl]-pyridine,
2,5-bis[1,1-di(hydroxymethyl)-1-ethyloxymethyl]-pyridine,
2,6-bis[1,1-di(hydroxymethyl)-1-ethyloxymethyl]-pyridine,
3,5-bis[1,1-di(hydroxymethyl)-1-ethyloxymethyl]-pyridine,
bis-N,N'-(2-hydroxyethylamido)-2,5-pyrazine,
bis-N,N'-(2-hydroxyethylamido)-2,6-pyrazine,
bis[N-methyl(2-hydroxyethylamido)]-2,5-pyrazine,
bis[N-methyl(2-hydroxyethylamido)]-2,6-pyrazine,
bis(2,3-dihydroxy-1-propylamido)-2,5-pyrazine,
bis(2,3-dihydroxy-1-propylamido)-2,6-pyrazine,
bis[N-methyl(2,3-dihydroxy-1-propylamido)]-2,5-pyrazine,
bis[N-methyl(2,3-dihydroxy-1-propylamido)]-2,6-pyrazine,
bis[N-methyl-(1,3-dihydroxy-2-propylamido)]-2,5-pyrazine,
bis[N-methyl(1,3-dihydroxy-2-propylamido)]-2,6-pyrazine,
bis(2 3,4-trihydroxy-1-butylamido)-2,5-pyrazine,
bis(2,3,4-trihydroxy-1-butylamido)-2,6-pyrazine,
bis[N-methyl[(2,3,4-trihydroxy-1-butylamido)]-2,5-pyrazine,
bis[N-methyl[(2,3,4-trihydroxy-1-butylamido)]-2,6-pyrazine,
bis(1,3,4-trihydroxy-2-butylamido)-2,5-pyrazine,
bis(1,3,4-trihydroxy-2-butylamido)-2,6-pyrazine,
bis[N-methyl[(1,3,4-trihydroxy-2-butylamido)]-1-2,5-pyrazine,
bis[N-methyl[(1,3,4-trihydroxy-2-butylamido)]-1-2,6-pyrazine,
bis[2-(hydroxymethyl)-3-hydroxy-1-propylamido)-2,5-pyrazine,
bis[2-(hydroxymethyl)-3-hydroxy-1-propylamido)-2,6-pyrazine,
bis{[N-methyl-2-(hydroxymethyl)-3-hydroxy-1-propylamido]}-2,5-pyrazine,
bis{[N-methyl-2-(hydroxymethyl)-3-hydroxy-1-propylamido]}-2,6-pyrazine, bis[1,1,1-tri(hydroxymethyl)methylamido]-2,5-pyrazine,
bis[1,1,1-tri(hydroxymethyl)methylamido]-2,6-pyrazine,
bis{[N-methyl[1,1,1-tri(hydroxymethyl)methylamido]}-2,5-pyrazine,
bis{[N-methyl[1,1,1-tri(hydroxymethyl)methylamido]}-2,6-pyrazine,
bis[1,1-di(hydroxymethyl)-1-ethylamido]-2,5-pyrazine,
bis[1,1-di(hydroxymethyl)-1-ethylamido]-2,6-pyrazine,
bis{[N-methyl[1,1-di(hydroxymethyl)-1-ethylamido]}-2,5-pyrazine,
bis{[N-methyl[1,1-di(hydroxymethyl)-1-ethylamido]}-2,6-pyrazine,
bis-N,N'-(2-hydroxyethylamido)-2,5-pyridine,
bis-N,N'-(2-hydroxyethylamido)-2,6-pyridine,
bis-N,N'-(2-hydroxyethylamido)-3,5-pyridine,
bis[N-methyl(2-hydroxyethylamido)]-2,5-pyridine,
bis[N-methyl(2-hydroxyethylamido)]-2,6-pyridine,
bis[N-methyl(2-hydroxyethylamido)]-3,5-pyridine,
bis(2,3-dihydroxy-1-propylamido)-2,5-pyridine,
bis(2,3-dihydroxy-1-propylamido)-2,6-pyridine,
bis(2,3-dihydroxy-1-propylamido)-3,5-pyridine,
bis[N-methyl(2,3-dihydroxy-1-propylamido)]-2,5-pyridine,
bis[N-methyl(2,3-dihydroxy-1-propylamido)]-2,6-pyridine,
bis[N-methyl(2,3-dihydroxy-1-propylamido)]-3,5-pyridine,
bis[N-methyl(1,3-dihydroxy-2-propylamido)]-2,5-pyridine,
bis[N-methyl(1,3-dihydroxy-2-propylamido)]-2,6-pyridine,
bis[N-methyl(1,3-dihydroxy-2-propylamido)]-3,5-pyridine,
bis(2,3,4-trihydroxy-1-butylamido)-2,5-pyridine,
bis(2,3,4-trihydroxy-1-butylamido)-2,6-pyridine,
bis(2,3,4-trihydroxy-1-butylamido)-3,5-pyridine,
bis[N-methyl(2,3,4-trihydroxy-1-butylamido)]-2,5-pyridine,
bis[N-methyl(2,3,4-trihydroxy-1-butylamido)]-2,6-pyridine,
bis[N-methyl(2,3,4-trihydroxy-1-butylamido)]-3,5-pyridine,
bis(1,3,4-trihydroxy-2-butylamido)-2,5-pyridine,
bis(1,3,4-trihydroxy-2-butylamido)-2,6-pyridine,
bis(1,3,4-trihydroxy-2-butylamido)-3,5-pyridine,
bis[N-methyl(1,3,4-trihydroxy-2-butylamido)]-2,5-pyridine,
bis[N-methyl(1,3,4-trihydroxy-2-butylamido)]-2,6-pyridine,
bis[N-methyl(1,3,4-trihydroxy-2-butylamido)]-3,5-pyridine,
bis[2-(hydroxymethyl)-3-hydroxy-1-propylamido]-2,5-pyridine,
bis[2-(hydroxymethyl)-3-hydroxy-1-propylamido]-2,6-pyridine,
bis[2-(hydroxymethyl)-3-hydroxy-1-propylamido]-3,5-pyridine,
bis{[N-methyl[2-(hydroxymethyl)-3-hydroxy-1-propylamido]}-2,5-pyridine,
bis{[N-methyl[2-(hydroxymethyl)-3-hydroxy-1-propylamido]}-2,6-pyridine,
bis{[N-methyl[2-(hydroxymethyl)-3-hydroxy-1-propylamido]}-3,5-pyridine,
bis[1,1,1-tri(hydroxymethyl)methylamido]-2,5-pyridine,
bis[1,1,1-tri(hydroxymethyl)methylamido]-2,6-pyridine,
bis[1,1,1-tri(hydroxymethyl)methylamido]-3,5-pyridine,
bis{[N-methyl[1,1,1-tri(hydroxymethyl)methylamido]}-2,5-pyridine,
bis{[N-methyl-[1,1,1-tri(hydroxymethyl)methylamido]}-2,6-pyridine,
bis{[N-methyl[1,1,1-tri(hydroxymethyl)methylamido]}-3,5-pyridine,
bis[1,1-di(hydroxymethyl)-1-ethylamido]-2,5-pyridine,
bis[1,1-di(hydroxymethyl)-1-ethylamido]-2,6-pyridine,
bis[1,1-di(hydroxymethyl)-1-ethylamido]-3,5-pyridine,
bis{[N-methyl[1,1-di(hydroxymethyl)-1-ethylamido]}-2,5-pyridine,
bis{[N-methyl[1,1-di(hydroxymethyl)-1-ethylamido]}-2,6-pyridine, and
bis{[N-methyl[1,1-di(hydroxymethyl)-1-ethylamido]}-3,5-pyridine, stereoisomers of these compounds or salts of these compounds with a pharmaceutically acceptable inorganic or organic acid.

3. A pharmaceutical composition according to claim 1, in which, in formula (I), R represents a nitrogen atom, $R_1$ and $R_3$ each represent the same radical selected from the group consisting of —CO—$NR_5R_6$, —CO—N($CH_2$—(CHOH)$_n$—$CH_2OH$)$_2$, in which n is equal to 0, 1, 2, 3 or 4, —$CH_2$—$NR_5R_6$, —$CH_2$—N($CH_2$—(CHOH)$_y$—$CH_2OH$)$_2$ in which y is equal to 0, 1, 2, 3 or 4, $R_2$ and $R_4$ each represent a hydrogen atom, $R_5$ represents a hydrogen atom or an alkyl radical and $R_6$ represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$ or —C($CH_2OH$)$_3$, stereoisomers thereof and salts thereof with a pharmaceutically acceptable inorganic or organic acid.

4. A pharmaceutical composition according to claim 1, which contains a compound selected from the group consisting of:

N,N'-bis[(tris(hydroxymethyl)methyl]pyrazine-2,5-dicarboxamide,
N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dicarboxamide,
N,N'-bis(1,3-dihydroxy-2-propyl)pyrazine-2,5-dicarboxamide,
N,N'-bis(2,3-dihydroxy-1-propyl)pyrazine-2,5-dicarboxamide,
N,N,N',N'-tetrakis(2-hydroxyethyl)pyrazine-2,5-dicarboxamide,
bis{N-[2(R,S)-3-dihydroxy-1-propyl]-N-methyl}pyrazine-2,5-dicarboxamide,
N,N'-bis(2-methoxyethyl)pyrazine-2,5-dicarboxamide,
N,N'-bis(2-hydroxyethyloxyethyl)pyrazine-2,5-dicarboxamide,
N,N'-bis(1,3-dihydroxy-2-propyl)pyridine-2,6-dicarboxamide,
N,N'-bis(1,3-dihydroxy-2-methyl-2-propyl)pyridine-2,6-dicarboxamide,
N,N'-bis(1,3-dihydroxy-2-propyl)pyridine-3,5-dicarboxamide,
N,N'-bis(1,3-dihydroxy-2-propyl)pyrazine-2,5-dimethanamine,
N,N,N',N'-tetrakis(2-hydroxyethyl)pyrazine-2,5-dimethanamine,
N,N'-bis(1,3-dihydroxy-2-propyl)pyrazine-2,5-dimethanamine,
N,N'-(1,3-dihydroxy-2-methyl-2-propyl)pyridine-2,6-dimethanamine,
N,N'-(1,3-dihydroxy-2-propyl)pyridine-2,6-dimethanamine,
2,5-bis[N,N'-(3-methoxy-1-propylamido)]pyridine,
2,6-bis(2-methoxyethyloxymethyl)pyridine,
N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5 dimethanamine, and
2,6-bis[N,N'-(1,3-dihydroxy-2-methyl-2-propylamido)]-pyridine-2,6-bis[N,N'-(1,3-dihydroxy-2-methyl-2-propylamido)]pyridine, stereoisomers thereof and salts thereof with a pharmaceutically acceptable inorganic or organic acid.

5. A compound of formula:

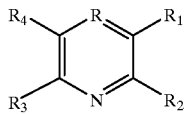

(I)

in which

R represents a nitrogen atom, $R_1$ and $R_3$ each represent the same radical selected from the group consisting of —CO—$NR_5R_6$, —CO—N(CH($CH_2OH$)$_2$)$_2$, —CO—N($CH_2OH$)$_2$, —CO—N($CH_2$—CH($CH_2OH$)$_2$)$_2$, —CO—N($CH_2$—(CHOH)$_n$—$CH_2OH$)$_2$ in which n is equal to 0, 1, 2, 3 or 4, —$CH_2$—O—$R_6$, —$NR_5$—CO—$R_6$, —$CH_2$—$NR_5R_6$, —$CH_2$—N($CH_2OH$)$_2$, —$CH_2$—N($CH_2$—(CHOH)$_y$—$CH_2OH$)$_2$ in which y is equal to 0, 1, 2, 3, or 4, —$CH_2$—N(CH($CH_2OH$)$_2$)$_2$ and —$CH_2$—N($CH_2$—CH($CH_2OH$)$_2$)$_2$ and $R_2$ and $R_4$ each represents a hydrogen atom, $R_5$ represents a hydrogen atom or an alkyl radical, $R_6$ represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$, —C($CH_2OH$)$_3$, —C($CH_3$)($CH_2OH$)$_2$, —$CH_2$—CH($CH_2OH$)$_2$ or —CH($CH_2OH$)(CHOH)$_x$—$CH_2OH$ in which x is equal to 1, 2, 3 or 4, alk represents an alkyl radical, the alkyl radicals containing, unless otherwise stated, 1 to 6 carbon atoms in a straight or branched chain, their stereoisomers and their salts with an inorganic or organic acid.

6. A compound according to claim 5, in which

R represents a nitrogen atom, $R_1$ and $R_3$ each represent the same radical selected from the group consisting of —CO—$NR_5R_6$, —CO—N($CH_2$—(CHOH)$_n$—$CH_2OH$)$_2$ in which n is equal to 0, 1, 2, 3 or 4, —$CH_2$—$NR_5R_6$, and —$CH_2$—N($CH_2$—(CHOH)$_y$—$CH_2OH$)$_2$ in which y is equal to 0, 1, 2, 3 or 4, $R_2$ and $R_4$ —$CH_2$—$NR_5R_6$, and —$CH_2$—N($CH_2$—(CHOH)$_y$—$CH_2OH$)$_2$ in which y is equal to 0, 1, 2, 3 or 4, each represent a hydrogen atom, $R_5$ represents a hydrogen atom or an alkyl radical and $R_6$ represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$ or —C($CH_2OH$)$_3$, alk represents an alkyl radical, the alkyl radicals containing, except where otherwise mentioned, 1 to 6 carbon atoms in a straight or branched chain, their stereoisomers and their salts with a pharmaceutically acceptable inorganic or organic acid.

7. A compound according to claim 5, selected from the-group consisting of:

N,N'-bis[(tris(hydroxymethyl)methyl]pyrazine-2,5-dicarboxamide,
N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dicarboxamide,
N,N'-bis(1,3-dihydroxy-2-propyl)pyrazine-2,5-dicarboxamide,
N,N'-bis(2,3-dihydroxy-1-propyl)pyrazine-2,5-dicarboxamide,
N,N,N',N'-tetrakis(2-hydroxyethyl)pyrazine-2,5-dicarboxamide,
bis{N-[2(R,S)-3-dihydroxy-1-propyl]-N-methyl}pyrazine-2,5-dicarboxamide,
N,N'-bis(2-methoxyethyl)pyrazine-2,5-dicarboxamide,
N,N'-bis(2-hydroxyethyloxyethyl)pyrazine-2,5-dicarboxamide,
N,N'-bis(1,3-dihydroxy-2-propyl)pyridine-2,6-dicarboxamide,
N,N'-bis(1,3-dihydroxy-2-methyl-2-propyl)pyridine-2,6-dicarboxamide,
N,N'-bis(1,3-dihydroxy-2-propyl)pyridine-3,5-dicarboxamide,
N,N'-bis(1,3-dihydroxy-2-propyl)pyrazine-2,5-dimethanamine,
N,N,N',N'-tetrakis(2-hydroxyethyl)pyrazine-2,5-dimethanamine,
N,N'-bis(1,3-dihydroxy-2-propyl)pyrazine-2,5-dimethanamine,
N,N'-(1,3-dihydroxy-2-methyl-2-propyl)pyridine-2,6-dimethanamine,
N,N'-(1,3-dihydroxy-2-propyl)pyridine-2,6-dimethanamine,
2,5-bis[N,N'-(3-methoxy-1-propylamido)]pyridine,
2,6-bis(2-methoxyethyloxymethyl)pyridine,
N-methyl-N-[(2S,3R,4R,5R)-2,3,4,5-tetrahydroxy-1-hexyl]-N'-methyl-N'-[(2S,3R,4R,5R)-2,3,4,5-tetrahydroxy-1-hexyl]pyrazine-2,5-dimethanamine,
2,6-bis[N,N'-(1,3-dihydroxy-2-methyl-2-propylamido)]-pyridine-2,6-bis[N,N'-(1,3-dihydroxy-2-methyl-2-propylamido)]pyridine and their salts with an inorganic or organic acid.

8. A process for the preparation of a compound according to claim 5, wherein R represents a nitrogen atom, $R_1$ and $R_3$ each represent the same radical selected from the group consisting of —CO—$NR_5R_6$, —CO—N(CH($CH_2OH$)$_2$)$_2$, —CO—N($CH_2OH$)$_2$, —CO—N($CH_2$—CH($CH_2OH$)$_2$)$_2$, and —CO—N($CH_2$—(CHOH)$_n$—$CH_2OH$)$_2$, and $R_2$ and $R_4$ each represent a hydrogen atom, said process comprising reacting a derivative of formula:

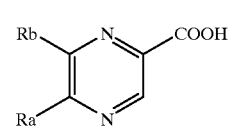

(II)

in which one of the substituents Ra and Rb represents a carboxyl radical and the other represents a hydrogen atom, or a reactive derivative of this diacid, with an amine, HNRcRd (III) in which either Rc represents a hydrogen atom or an alkyl radical and Rd represents a radical —$CH_2$—(CHOH)m—$CH_2OH$ in which m is equal to 0, 1, 2, 3 or 4, -alk-O-alk-$CH_2OH$, -alk-O-alk, —CH($CH_2OH$)$_2$, —C($CH_2OH$)$_3$, —C($CH_3$)($CH_2OH$)$_2$, —$CH_2$—CH($CH_2OH$)$_2$ or —CH($CH_2OH$)(CHOH)$_x$—$CH_2OH$ in which x is equal to 1, 2, 3 or 4 and alk represents an alkyl radical, or Rc and Rd are identical and each represent a radical —$CH_2$—(CHOH)$_n$—$CH_2OH$ in which n is equal to 0, 1, 2, 3 or 4, —CH($CH_2OH$)$_2$, —$CH_2OH$ or —$CH_2$—CH($CH_2OH$)$_2$, the alkyl radicals containing 1 to 6 carbon atoms in a straight or branched chain, isolating the product and optionally converting it into a salt with an inorganic or organic acid.

9. A method for the treatment or prevention of diabetes, this method comprising administering to a patient in need of such treatment an effective amount of a compound of formula

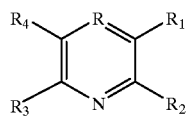

in which
- R represents a nitrogen atom, $R_1$ and $R_3$ each represent the same radical selected from the group consisting of —CO—$NR_5R_6$, —CO—$N(CH(CH_2OH)_2)_2$, —CO—$N(CH_2OH)_2$, —CO—$N(CH_2$—$CH(CH_2OH)_2)_2$, —CO—$N(CH_2$—$(CHOH)_n$—$CH_2OH)_2$ in which n is equal to 0, 1, 2, 3 or 4, —$CH_2$—O—$R_6$, —$NR_5$—CO—$R_6$, —$CH_2$—$NR_5R_6$, —$CH_2$—$N(CH_2OH)_2$, —$CH_2$—$N(CH_2$—$(CHOH)_y$—$CH_2OH)_2$ in which y is equal to 0, 1, 2, 3 or 4, —$CH_2$—$N(CH(CH_2OH)_2)_2$ and —$CH_2$—$N(CH_2$—$CH(CH_2OH)_2)_2$ and $R_2$ and $R_4$ each represent a hydrogen atom,
- $R_5$ represents a hydrogen atom or an alkyl radical,
- $R_6$ represents a radical —$CH_2$—$(CHOH)m$—$CH_2OH$ in which m is equal to 0, 1, 2, 3 or 4, -alk-O-alk-$CH_2OH$, -alk-O-alk, —$CH(CH_2OH)_2$, —$C(CH_2OH)_3$, —$C(CH_3)(CH_2OH)_2$, —$CH_2$—$CH(CH_2OH)_2$ or —CH$(CH_2OH)$—$(CHOH)_x$—$CH_2OH$ in which x is equal to 1, 2, 3 or 4,
- alk represents an alkyl radical, the alkyl radicals containing, unless otherwise stated, 1 to 6 carbon atoms in a straight or branched chain, their stereoisomers and their salts with an inorganic or organic acid, in a pharmaceutically acceptable vehicle.

* * * * *